United States Patent
Blankenstein et al.

(10) Patent No.: US 12,421,290 B2
(45) Date of Patent: Sep. 23, 2025

(54) CD22-SPECIFIC T CELL RECEPTORS AND ADOPTIVE T CELL THERAPY FOR TREATMENT OF B CELL MALIGNANCIES

(71) Applicants: MAX-DELBRÜCK-CENTRUM FÜR MOLEKULARE MEDIZIN IN DER HELMHOLTZ-GEMEINSCHAFT, Berlin (DE); CHARITÉ—UNIVERSITÄTSMEDIZIN BERLIN, Berlin (DE)

(72) Inventors: Thomas Blankenstein, Berlin (DE); Antonio Pezzutto, Berlin (DE); Simone Rhein, Berlin (DE)

(73) Assignees: MAX-DELBRÜCK-CENTRUM FÜR MOLEKULARE MEDIZIN IN DER, Berlin (DE); HELMHOLTZ-GEMEINSCHAFT; CHARITÉ—UNIVERSITÄTSMEDIZIN BERLIN, Berlin (DE)

( * ) Notice: Subject to any disclaimer, the term of this patent is extended or adjusted under 35 U.S.C. 154(b) by 1135 days.

(21) Appl. No.: 17/414,471

(22) PCT Filed: Dec. 17, 2019

(86) PCT No.: PCT/EP2019/085765
§ 371 (c)(1),
(2) Date: Jun. 16, 2021

(87) PCT Pub. No.: WO2020/127357
PCT Pub. Date: Jun. 25, 2020

(65) Prior Publication Data
US 2022/0064256 A1    Mar. 3, 2022

(30) Foreign Application Priority Data
Dec. 18, 2018   (EP) .................................... 18213482

(51) Int. Cl.
| | | |
|---|---|---|
| *C07K 14/725* | (2006.01) | |
| *A61K 38/00* | (2006.01) | |
| *A61P 35/00* | (2006.01) | |
| *C07K 14/705* | (2006.01) | |
| *C07K 14/71* | (2006.01) | |

(52) U.S. Cl.
CPC .......... *C07K 14/7051* (2013.01); *A61P 35/00* (2018.01); *C07K 14/70596* (2013.01); *C07K 14/71* (2013.01); *A61K 38/00* (2013.01)

(58) Field of Classification Search
None
See application file for complete search history.

(56) References Cited

U.S. PATENT DOCUMENTS 10,202,640 B2 *   2/2019   Davis ............... C12Q 1/686
2015/0337369 A1   11/2015  Davis et al.

FOREIGN PATENT DOCUMENTS

| NO | 2012/079000 | 6/2012 | |
|---|---|---|---|
| WO | 2008/108257 | 9/2008 | |
| WO | 2008/108257 A1 | 9/2008 | |
| WO | 2013/059593 | 4/2013 | |
| WO | 2014/011518 | 1/2014 | |
| WO | 2017/0184590 A1 | 10/2017 | |
| WO | 2018/200582 | 11/2018 | |
| WO | WO-2018200582 A1 * | 11/2018 | ............. A61K 35/17 |

OTHER PUBLICATIONS

Ellis et al. Frequencies of HLA-A2 Alleles in Five U.S. Population GroupsHuman Immunol, 2000; 61:334-340. (Year: 2000).*
Jahn et al. A CD22-reactive TCR from the T-cell allorepertoire for the treatment of acute lymphoblastic leukemia by TCR gene transfer. Oncotarget, 2016; 7(44):71536-71547. (Year: 2016).*
Rosati et al. Overview of methodologies for T-cell receptor repertoire analysis. 2017; 17(61): 1-16. (Year: 2017).*
Dorner et al. "The mechanistic impact of CD22 engagement with epratuzumab on B cell function: Implications for the treatment of systemic lupus erythematosus", Autoimmunity Reviews (2015) 14: 1079-1086.
Tuscano et al. "The Bs20x22 anti-CD20-CD22 bispecific antibody has more lymphomacidal activity than do the parent antibodies alone", Cancer Immunol Immunother (2011) 60: 771-780.
Dang et al. "Randomized, phase 3 trial of inotuzumab ozogamicin plus rituximab versus chemotherapy plus rituximab for relapsed/refractory aggressive B-cell non-Hodgkin lymphoma", British Journal of Haematology (2018) 182: 583-586.
Fry et al. "CD22-targeted Car T cells induce remission in B-ALL that is naive or resistant to CD19-targeted CAR Immunotherapy", Nature Medicine (2018) 24: 20-28.
Danska et al. "The Presumptive CDR3 Regions of Both T Cell Receptor a and B Chains Determine T Cell Specificity for Myoglobin Peptides", J. Exp. Med. (1990) 172: 27-33.
Garcia et al. "How the T Cell Receptor Sees Antigen - A Structural View", Cell (2005) 122(3): 333-336.
Chervin et al. "Engineering higher affinity T cell receptors using a T cell display system", Journal of Immunological Methods (2008) 339: 175-184.
Linette et al. "Cardiovascular toxicity and titin cross-reactivity of affinity-enhanced T cells in myeloma and melanoma", Blood (2013) 122(6): 863-871.

(Continued)

*Primary Examiner* — Daniel E Kolker
*Assistant Examiner* — Maureen Varina Driscoll
(74) *Attorney, Agent, or Firm* — Meunier Carlin & Curfman LLC

(57) ABSTRACT

The present invention is directed to the field of immunotherapy, in particular, adoptive T cell therapy or T cell receptor (TCR) gene therapy of cancer, in particular, of B cell lymphoma or B cell leukemia. The invention provides a nucleic acid encoding TCR alpha or beta chain constructs of TCR constructs capable of specifically binding to a peptide of SEQ ID NO: 1, derived from the lineage specific antigen CD22, in the context of HLA-A2 and to subsequently lyse CD22-positive cells. The invention further provides a corresponding protein and host cell. e.g., a CD8+ T cell, pharmaceutical compositions comprising the same, and therapeutic use for treatment of B cell lymphoma or B cell leukemia, such as diffuse large B-cell lymphoma (DLBCL).

Figure 1:
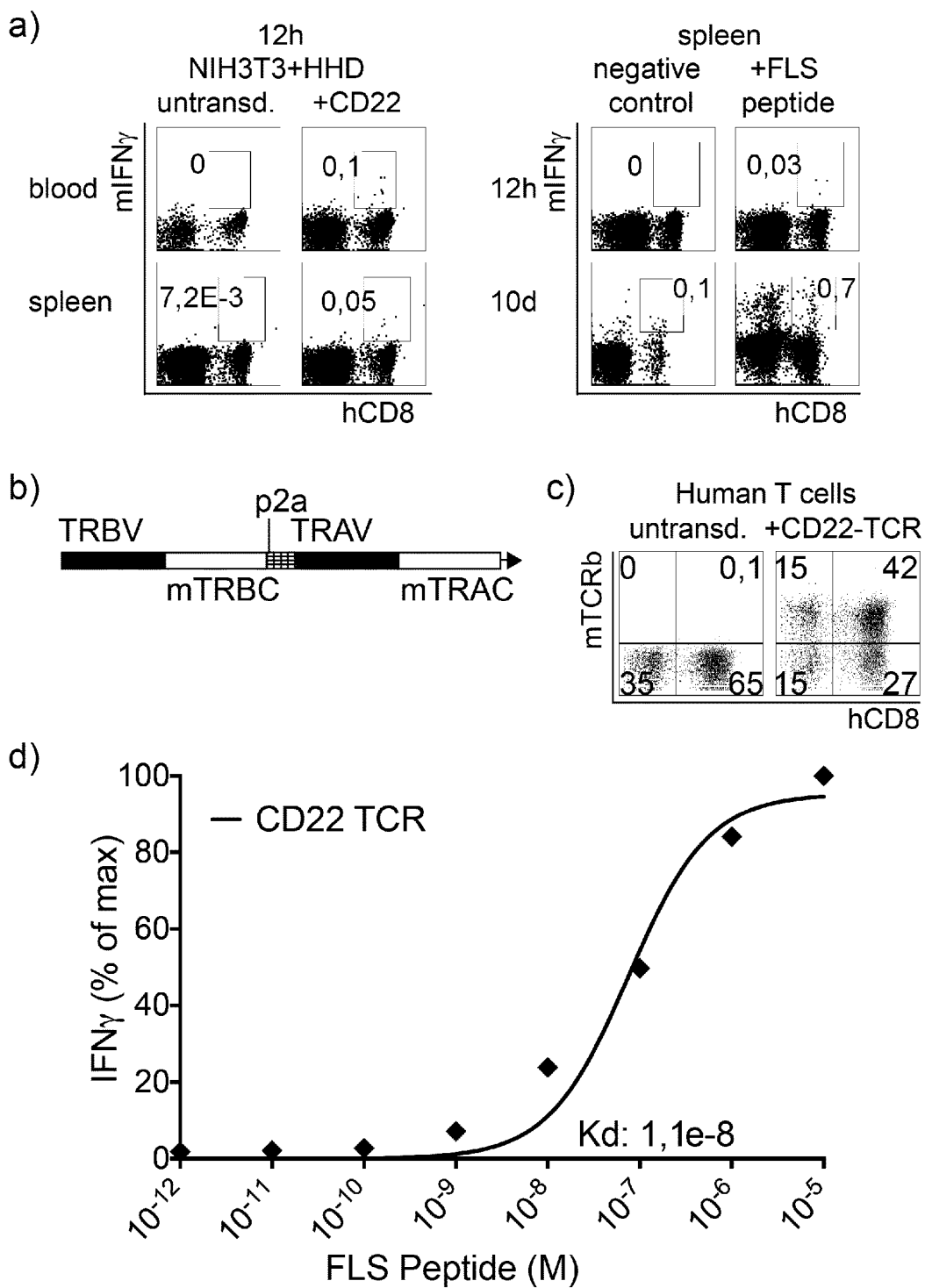

23 Claims, 8 Drawing Sheets
Specification includes a Sequence Listing.

(56) References Cited

OTHER PUBLICATIONS

Morgan et al. "Cancer Regression and Neurological Toxicity Following Anti-MAGE-A3 TCR Gene Therapy", J. Immunother (2013) 36: 133-151.
Kuball et al. "Facilitating matched pairing and expression of TCR chains introduced into human T cells", Blood (2007) 106(6): 2331-2338.
Sommermeyer et al. "Minimal Amino Acid Exchange in Human TCR Constant Regions Fosters Improved Function of TCR Gene-Modified T Cells", The Journal of Immunology (2010) 184: 6223-6231.
Philip et al. "A highly compact epitope-based marker/suicide gene for easier and safer T-cell therapy", Blood (2014) 124(8): 1277-1287.
Paszkiewicz et al. "Targeted antibody-mediated depletion of murine CD19 Car T cells permanently reverses B cell aplasia", The Journal of Clinical Investigation (2016) 126(11): 4262-4272.
Wang et al. "A transgene-encoded cell surface polypeptide for selection, in vivo tracking, and ablation of engineered cells", Blood (2011) 118(5): 1255-1263.
Li et al. "Transgenic mice with a diverse human T cell antigen receptor repertoire", Nature Medicine (2010) 16: 1029-1035.
Tassan et al. "The Human Leukocyte Antigen-presented Ligandome of B Lymphocytes", Molecular & Cellular Proteomics (2013) 12(7): 1829-1843.
International Search Report and Written Opinion dated Mar. 19, 2020, from International Application No. PCT/ EP2019/085765, 11 pages.
Lorenz, J et al. "A CD22-reactive TCR from the T-cell allorepertoire for the treatment of acute lymphoblastic leukemia by TCR gene transfer", Oncotarget, vol. 7, No. 44, 12 pages.
James, S.T et al. "Antigen Sensitivity of CD22-Specific Chimeric TCR Is Modulated by Target Epitope Distance form the Cell Membrane", The Journal of Immunology, XP-002679899, 12 pages.
Robbins, P.F et al. "Singe and Duo Amino Acid Substitutions in TCR CDRs Can Enhance Antigen-Specific T Cell Functions", The Journal of Immunology, XP-002571412, 16 pages.
1 Communication Pursuant to Article P4(3) Epc issued for U.S. Appl. No. 19/827,696, dated Jul. 26, 2022.
Bardi et al. "Hla-A, B and DRBI allele and baplotype frequencies in volunteer bone marrow donors from the north of Parana State," Rev Bros Hematol Hemoter 2012;34{1):25-30.

* cited by examiner c)

a)

SEQUENCE LISTING

<160> NUMBER OF SEQ ID NOS: 27

<210> SEQ ID NO 1
<211> LENGTH: 9
<212> TYPE: PRT
<213> ORGANISM: Homo sapiens
<220> FEATURE:
<223> OTHER INFORMATION: FLS peptide: CD22 epitope

<400> SEQUENCE: 1

Phe Leu Ser Asn Asp Thr Val Gln Leu
1               5

<210> SEQ ID NO 2
<211> LENGTH: 6
<212> TYPE: PRT
<213> ORGANISM: Homo sapiens
<220> FEATURE:
<223> OTHER INFORMATION: alpha chain CDR1

<400> SEQUENCE: 2

Val Thr Asn Phe Arg Ser
1               5

<210> SEQ ID NO 3
<211> LENGTH: 7
<212> TYPE: PRT
<213> ORGANISM: Homo sapiens
<220> FEATURE:
<223> OTHER INFORMATION: alpha chain CDR2

<400> SEQUENCE: 3

Leu Thr Ser Ser Gly Ile Glu
1               5

<210> SEQ ID NO 4
<211> LENGTH: 12
<212> TYPE: PRT
<213> ORGANISM: Homo sapiens
<220> FEATURE:
<223> OTHER INFORMATION: alpha chain CDR3

<400> SEQUENCE: 4

Cys Ala Val Asp Asn Gln Gly Gly Lys Leu Ile Phe
1               5                   10

<210> SEQ ID NO 5
<211> LENGTH: 6
<212> TYPE: PRT
<213> ORGANISM: Homo sapiens
<220> FEATURE:
<223> OTHER INFORMATION: beta chain CDR1

<400> SEQUENCE: 5

Asp Phe Gln Ala Thr Thr
1               5

<210> SEQ ID NO 6
<211> LENGTH: 7
<212> TYPE: PRT
<213> ORGANISM: Homo sapiens
<220> FEATURE:
<223> OTHER INFORMATION: beta chain CDR2

<400> SEQUENCE: 6

Ser Asn Glu Gly Ser Lys Ala
1               5

<210> SEQ ID NO 7
<211> LENGTH: 14
<212> TYPE: PRT
<213> ORGANISM: Homo sapiens
<220> FEATURE:
<223> OTHER INFORMATION: beta chain CDR3

<400> SEQUENCE: 7

Cys Ser Ala Arg Pro Ser Gly Val Tyr Asn Glu Gln Phe Phe
1               5                   10

<210> SEQ ID NO 8
<211> LENGTH: 411
<212> TYPE: DNA
<213> ORGANISM: Artificial Sequence
<220> FEATURE:
<223> OTHER INFORMATION: murine constant region of TCR alpha - codon-
      optimized

<400> SEQUENCE: 8
aacatccaga accccgagcc cgccgtgtac cagctgaagg accccagaag ccaggacagc    60
accctgtgcc tgttcaccga cttcgacagc cagatcaacg tgcccaagac catggaaagc   120
ggcaccttca tcaccgacaa gacagtgctg gacatgaagg ccatggacag caagagcaac   180
ggcgccattg cctggtccaa ccagaccagc ttcacatgcc aggacatctt caaagagaca   240
aacgccacct accccagcag cgacgtgccc tgcgacgcca ccctgaccga aagagcttc    300 gagacagaca tgaacctgaa tttccagaac ctgagcgtga tgggcctgcg gatcctgctg   360
ctgaaggtgg ccggcttcaa cctgctgatg accctgcggc tgtggagcag c            411

<210> SEQ ID NO 9
<211> LENGTH: 423
<212> TYPE: DNA
<213> ORGANISM: Artificial Sequence
<220> FEATURE:
<223> OTHER INFORMATION: minimally murinized constant region - TCR alpha

<400> SEQUENCE: 9
aacatccaga accccgaccc cgccgtgtat cagctgagag acagcaagag cagcgacaag    60
tccgtgtgcc tgttcaccga cttcgacagc cagaccaatg tgtcccagtc caaggacagc   120
gacgtgtaca tcaccgacaa gaccgtgctg gacatgcgca gcatggactt caagagcaac   180
tccgccgtgg cctggtccaa caagagcgat ttcgcctgcg ccaacgcctt caacaacagc   240
attatccccg aggacacatt cttcccaagc tcagacgttc cctgcgacgt gaagctggtg   300
gaaaagagct tcgagacaga caccaacctg aacttccaga acctgagcgt gatcggcttc   360
cggatcctgc tgctgaaggt ggccggcttc aacctgctga tgaccctgag actgtggtcc   420
agc                                                                  423

<210> SEQ ID NO 10
<211> LENGTH: 423
<212> TYPE: DNA
<213> ORGANISM: Artificial Sequence
<220> FEATURE:
<223> OTHER INFORMATION: human constant region TCR alpha - codon-
      optimized

<400> SEQUENCE: 10
aacatccaga accccgaccc cgccgtgtat cagctgagag acagcaagag cagcgacaag    60
tccgtgtgcc tgttcaccga cttcgacagc cagaccaatg tgtcccagtc caaggacagc   120

```
gacgtgtaca tcaccgacaa gaccgtgctg gacatgcgca gcatggactt caagagcaac    180
tccgccgtgg cctggtccaa caagagcgat ttcgcctgcg ccaacgcctt caacaacagc    240
attatccccg aggacacatt cttcccaagc cccgagagca gctgcgacgt gaagctggtg    300
gaaaagagct cgagacaga caccaacctg aacttccaga acctgagcgt gatcggcttc    360
cggatcctgc tgctgaaggt ggccggcttc aacctgctga tgaccctgag actgtggtcc    420
agc                                                                  423
```

<210> SEQ ID NO 11
<211> LENGTH: 519
<212> TYPE: DNA
<213> ORGANISM: Artificial Sequence
<220> FEATURE:
<223> OTHER INFORMATION: murine constant region TCR beta - codon
      optimized

<400> SEQUENCE: 11

```
gaagatctga ggaacgtgac cccacccaag gtgtccctgt tcgagcccag caaggccgag     60
atcgccaaca agcagaaagc caccctggtc tgcctggcca ggggcttctt ccccgaccac    120
gtggagctgt cttggtgggt gaacggcaaa gaggtgcaca gcggagtcag taccgacccc    180
caggcctaca agagagcaa ctacagctac tgcctgagca gcaggctgag agtgagcgcc    240
accttctggc acaaccccg gaaccacttc cggtgccagg tgcagttcca cggcctgagc    300
gaagaggaca gtggcctga gggcagcccc aagcccgtga cccagaacat cagcgccgag    360
gcctggggca gagccgactg cggcatcacc agcgccagct accaccaggg cgtgctgtcc    420
gccaccatcc tgtacgagat cctgctgggc aaggccaccc tgtacgccgt gctggtgtcc    480
ggcctggtgc tgatggccat ggtgaagaag aagaacagc                           519
```

<210> SEQ ID NO 12
<211> LENGTH: 537
<212> TYPE: DNA
<213> ORGANISM: Artificial Sequence
<220> FEATURE:
<223> OTHER INFORMATION: minimally murinized constant region TCR beta
      codon-optimized

<400> SEQUENCE: 12

```
gaggatctga agaacgtgtt cccccagag gtggccgtgt cgagccttc taaagccgag      60 atcgcacaca cccagaaagc caccctcgtg tgtctggcca ccggcttcta ccccgaccat    120
gtggaactgt cttggtgggt caacggcaaa gaggtgcaca gcggagtgtc caccgacccc    180
cagcctctga agaacagcc cgccctgaac gacagccggt actgcctgag cagcagactg    240
agagtgtccg ccaccttctg gcagaacccc cggaaccact tcagatgcca ggtgcagttc    300
tacggcctga gcgagaacga cgagtggacc caggacagag ccaagcccgt gacccagatc    360
gtgtctgccg aagcctgggg cagagccgat tgcggcatca ccagcgcaag ctaccatcag    420
ggcgtgctga gcgccacaat cctgtacgag attctgctgg caaggccac actgtacgcc    480 gtgctggtgt ctgccctggt gctgatggcc atggtcaagc ggaaggacag cagaggc      537
```

<210> SEQ ID NO 13
<211> LENGTH: 537
<212> TYPE: DNA
<213> ORGANISM: Artificial Sequence
<220> FEATURE:
<223> OTHER INFORMATION: human constant region TCR beta - codon-
      optimized

<400> SEQUENCE: 13

```
gaggatctga agaacgtgtt cccccagag gtggccgtgt tcgagccttc tgaggccgag    60
atcagccaca cccagaaagc caccctcgtg tgtctggcca ccggcttcta ccccgaccat   120
gtggaactgt cttggtgggt caacggcaaa gaggtgcaca cgagtgtc caccgacccc    180
cagcctctga agaacagcc cgccctgaac gacagccggt actgcctgag cagcagactg   240
agagtgtccg ccaccttctg gcagaacccc cggaaccact tcagatgcca ggtgcagttc   300
tacggcctga gcgagaacga cgagtggacc caggacagag ccaagcccgt gacccagatc   360
gtgtctgccg aagcctgggg cagagccgat tgcggcttta ccagcgagag ctaccagcag   420
ggcgtgctga gcgccacaat cctgtacgag attctgctgg gcaaggccac actgtacgcc   480
gtgctggtgt ctgccctggt gctgatggcc atggtcaagc ggaaggacag cagaggc      537
```

<210> SEQ ID NO 14
<211> LENGTH: 390
<212> TYPE: DNA
<213> ORGANISM: Homo sapiens
<220> FEATURE:
<223> OTHER INFORMATION: aCD22 TCR alpha chain variable region
      TRAV36/DV7*04-TRAJ23*01 incl. leader

<400> SEQUENCE: 14

```
atgaagtgtc cacaggcttt actagctatc ttttggcttc tactgagctg ggtgagcagt    60
gaagacaagg tggtacaaag ccctctatct ctggttgtcc acgagggaga cactgtaact   120
ctcaattgca gttatgaagt gactaacttt cgaagcctac tatggtacaa gcaggaaaag   180
aaagctccca catttctatt tatgctaact tcaagtggaa ttgaaaagaa gtcaggaaga   240
ctaagtagca tattagataa gaaagaactt ttcagcatcc tgaacatcac agccacccag   300
accggagact cggccgtcta cctctgtgct gtggataacc agggaggaaa gcttatcttc   360
ggacagggaa cggagttatc tgtgaaaccc                                     390
```

<210> SEQ ID NO 15
<211> LENGTH: 390
<212> TYPE: DNA
<213> ORGANISM: Artificial Sequence
<220> FEATURE:
<223> OTHER INFORMATION: aCD22 TCR alpha chain variable region
      TRAV36/DV7*04-TRAJ23*01 - codon-optimized

<400> SEQUENCE: 15

```
atgaagtgcc cacaggccct gctggccatc ttttggctgc tgctgagctg ggtgtccagc    60
gaggacaagg tggtgcagag ccctctgagc ctggtggtgc acgagggcga taccgtgacc   120
ctgaattgca gctacgaagt gaccaacttc cggtccctgc tgtggtacaa gcaggaaaag   180
aaggccccca ccttcctgtt catgctgacc agcagcggca tcgagaagaa gtccggcaga   240
ctgtcctcca tcctggacaa gaaagagctg ttcagcatcc tgaatatcac cgccacccag   300
accggcgaca gcgccgtgta tctgtgcgcc gtggataacc agggcggcaa gctgatcttt   360
ggccagggca cagagctgag cgtgaagccc                                     390
```

<210> SEQ ID NO 16
<211> LENGTH: 130
<212> TYPE: PRT
<213> ORGANISM: Artificial Sequence
<220> FEATURE:
<221> NAME/KEY: SIGNAL
<222> LOCATION: 1..20

<220> FEATURE:
<223> OTHER INFORMATION: leader
<220> FEATURE:
<223> OTHER INFORMATION: aDC22 TCR alpha chain variable region
TRAV36/DV7*04-TRAJ23*01 incl. leader

<400> SEQUENCE: 16

```
Met Lys Cys Pro Gln Ala Leu Leu Ala Ile Phe Trp Leu Leu Leu Ser
 1               5                  10                  15

Trp Val Ser Ser Glu Asp Lys Val Val Gln Ser Pro Leu Ser Leu Val
            20                  25                  30

Val His Glu Gly Asp Thr Val Thr Leu Asn Cys Ser Tyr Glu Val Thr
        35                  40                  45

Asn Phe Arg Ser Leu Leu Trp Tyr Lys Gln Glu Lys Lys Ala Pro Thr
    50                  55                  60

Phe Leu Phe Met Leu Thr Ser Ser Gly Ile Glu Lys Lys Ser Gly Arg
65                  70                  75                  80

Leu Ser Ser Ile Leu Asp Lys Lys Glu Leu Phe Ser Ile Leu Asn Ile
                85                  90                  95

Thr Ala Thr Gln Thr Gly Asp Ser Ala Val Tyr Leu Cys Ala Val Asp
            100                 105                 110

Asn Gln Gly Gly Lys Leu Ile Phe Gly Gln Gly Thr Glu Leu Ser Val
        115                 120                 125

Lys Pro
   130
```

<210> SEQ ID NO 17
<211> LENGTH: 423
<212> TYPE: DNA
<213> ORGANISM: Homo sapiens
<220> FEATURE:
<223> OTHER INFORMATION: aCD22 TCR beta chain variable sequence
TRBV20-1-TRBJ2-1*01-TRBD2*01 incl. leader

<400> SEQUENCE: 17

```
atgggggaag gtggtgtgag gccatcacgg aagatgctgc tgcttctgct gcttctgggg     60
ccaggctccg ggcttggtgc tgtcgtctct caacatccga gctgggttat ctgtaagagt    120
ggaacctctg tgaagatcga gtgccgttcc ctggactttc aggccacaac tatgttttgg    180
tatcgtcagt ccccgaaaca gagtctcatg ctgatggcaa cttccaatga gggctccaag    240
gccacatacg agcaaggcgt cgagaaggac aagtttctca tcaaccatgc aagcctgacc    300
ttgtccactc tgacagtgac cagtgcccat cctgaagaca gcagcttcta catctgcagt    360
gctaggccta gcggggtcta caatgagcag ttcttcgggc cagggacacg gctcaccgtg    420
cta                                                                  423
```

<210> SEQ ID NO 18
<211> LENGTH: 423
<212> TYPE: DNA
<213> ORGANISM: Artificial Sequence
<220> FEATURE:
<223> OTHER INFORMATION: aCD22 TCR beta chain variable region
TRBV20-1-TRBJ2-1*01-TRBD2*01 incl. leader - codon optimized

<400> SEQUENCE: 18

```
atgggagaag gcggagtgcg gcctagccgg aagatgcttc tccttctgct gctgctgggc     60
cctggctctg gactgggagc tgtggtgtct cagcacccct cctgggtcat ctgcaagagc    120
ggcaccagcg tgaagatcga gtgcagaagc ctggacttcc aggccaccac catgttctgg    180
tacagacagt cccccaagca gagcctgatg ctgatggcca cctccaacga gggcagcaag    240
```

```
gccacatatg agcagggcgt ggaaaaggac aagttcctga tcaaccacgc cagcctgacc    300
ctgagcaccc tgacagtgac aagcgcccac cccgaggaca gcagcttcta catctgcagc    360
gccagaccca gcggcgtgta caacgagcag ttcttcggcc ctggcacccg gctgaccgtg    420
ctg                                                                  423
```

```
<210> SEQ ID NO 19
<211> LENGTH: 141
<212> TYPE: PRT
<213> ORGANISM: Artificial Sequence
<220> FEATURE:
<221> NAME/KEY: SIGNAL
<222> LOCATION: 1..25
<223> OTHER INFORMATION: Leader sequence aa12-25, TCR sequence starts at
      aa 26
<220> FEATURE:
<223> OTHER INFORMATION: aCD22 TCR beta chain variable region TRBV20-1-
      TRBJ2-1*01-TRBD2*01 incl. leader

<400> SEQUENCE: 19
```

Met Gly Glu Gly Gly Val Arg Pro Ser Arg Lys Met Leu Leu Leu
1               5                   10                  15

Leu Leu Leu Gly Pro Gly Ser Gly Leu Gly Ala Val Val Ser Gln His
            20                  25                  30

Pro Ser Trp Val Ile Cys Lys Ser Gly Thr Ser Val Lys Ile Glu Cys
        35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Pro Ser Gly Val Tyr Asn
        115                 120                 125

Glu Gln Phe Phe Gly Pro Gly Thr Arg Leu Thr Val Leu
    130                 135                 140

```
<210> SEQ ID NO 20
<211> LENGTH: 6
<212> TYPE: PRT
<213> ORGANISM: Homo sapiens
<220> FEATURE:
<223> OTHER INFORMATION: beta chain CDR1

<400> SEQUENCE: 20
```

Asp Phe Gln Ala Thr Thr
1               5

```
<210> SEQ ID NO 21
<211> LENGTH: 7
<212> TYPE: PRT
<213> ORGANISM: Homo sapiens
<220> FEATURE:
<223> OTHER INFORMATION: beta chain CDR2

<400> SEQUENCE: 21
```

Ser Asn Glu Gly Ser Lys Ala
1               5

<210> SEQ ID NO 22
<211> LENGTH: 14
<212> TYPE: PRT
<213> ORGANISM: Homo sapiens
<220> FEATURE:
<223> OTHER INFORMATION: 3225 TCR beta chain CDR3

<400> SEQUENCE: 22

Cys Ser Ala Arg Glu Ala Gly Val Tyr Asn Glu Gln Phe Phe
1               5                   10

<210> SEQ ID NO 23
<211> LENGTH: 390
<212> TYPE: DNA
<213> ORGANISM: Homo sapiens
<220> FEATURE:
<223> OTHER INFORMATION: 3225 TCR beta chain variable region
      TRBV20-1*01-TRBJ2-1*01-TRBD*02 F incl. leader
<220> FEATURE:
<221> NAME/KEY: sig_peptide
<222> LOCATION: 1..42
<223> OTHER INFORMATION: /function="leader peptide"

<400> SEQUENCE: 23

```
atgctgctgc ttctgctgct tctggggcca ggctccgggc ttggtgctgt cgtctctcaa     60
catccgagct gggttatctg taagagtgga acctctgtga agatcgagtg ccgttccctg    120
gactttcagg ccacaactat gttttggtat cgtcagttcc cgaaacagag tctcatgctg    180
atggcaactt ccaatgaggg ctccaaggcc acatacgagc aaggcgtcga aaggacaag     240 tttctcatca accatgcaag cctgaccttg tccactctga cagtgaccag tgcccatcct    300
gaagacagca gcttctacat ctgcagtgct agagaagcgg gagtctacaa tgagcagttc    360
ttcgggccag ggacacggct caccgtgcta                                      390
```

<210> SEQ ID NO 24
<211> LENGTH: 390
<212> TYPE: DNA
<213> ORGANISM: Artificial Sequence
<220> FEATURE:
<223> OTHER INFORMATION: 3225 TCR beta chain variable region codon-
      optimized TRBV20-1*01-TRBJ2-1*01-TRBD2*02 F
<220> FEATURE:
<221> NAME/KEY: sig_peptide
<222> LOCATION: 1..42
<223> OTHER INFORMATION: /function="leader peptide"

<400> SEQUENCE: 24

```
atgcttctcc ttctgctgct gctgggccct ggctctggac tgggagctgt ggtgtctcag     60 caccctcct gggtcatctg caagagcggc accagcgtga agatcgagtg cagaagcctg     120
gacttccagg ccaccaccat gttctggtac agacagttcc ccaagcagag cctgatgctg    180
atggccacct ccaacgaggg cagcaaggcc acatatgagc agggcgtgga aaaggacaag    240
ttcctgatca accacgccag cctgaccctg agcaccctga cagtgacaag cgcccacccc    300
gaggacagca gcttctacat ctgcagcgcc agagaagcgg gcgtgtacaa cgagcagttc    360
ttcggccctg gcacccggct gaccgtgctg                                      390
```

<210> SEQ ID NO 25
<211> LENGTH: 130
<212> TYPE: PRT
<213> ORGANISM: Homo sapiens
<220> FEATURE:
<221> NAME/KEY: SIGNAL
<222> LOCATION: 1..14
<223> OTHER INFORMATION: leader peptide

```
<220> FEATURE:
<223> OTHER INFORMATION: 3225 TCR beta chain variable region
      TRBV20-1*01-TRBJ2-1*01-TRBD2*02 F incl. leader

<400> SEQUENCE: 25

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
50                          55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Glu
            100                 105                 110

Ala Gly Val Tyr Asn Glu Gln Phe Phe Gly Pro Gly Thr Arg Leu Thr
            115                 120                 125

Val Leu
    130

<210> SEQ ID NO 26
<211> LENGTH: 42
<212> TYPE: DNA
<213> ORGANISM: Homo sapiens
<220> FEATURE:
<223> OTHER INFORMATION: 3225 beta chain construct CDR3 nt

<400> SEQUENCE: 26
tgcagtgcta gagaagcggg agtctacaat gagcagttct tc                        42

<210> SEQ ID NO 27
<211> LENGTH: 42
<212> TYPE: DNA
<213> ORGANISM: Artificial Sequence
<220> FEATURE:
<223> OTHER INFORMATION: 3225 beta chain construct CDR3 nt codon
      optimized

<400> SEQUENCE: 27
tgcagcgcca gagaagcggg cgtgtacaac gagcagttct tc                        42
```

CD22-SPECIFIC T CELL RECEPTORS AND ADOPTIVE T CELL THERAPY FOR TREATMENT OF B CELL MALIGNANCIES

The present invention is directed to the field of immunotherapy, in particular, adoptive T cell therapy or T cell receptor (TCR) gene therapy of cancer. The invention provides a nucleic acid encoding at least one TCR alpha or beta chain constructs of TCR constructs capable of specifically binding to a peptide of SEQ ID NO: 1, derived from the B cell lineage-specific antigen CD22, in the context of HLA-A*02:01. The invention also provides corresponding proteins and host cells, preferably, CD8+ T cells, expressing said TCR construct, as well as the medical use of such nucleic acids, proteins or host cells, in particular, in the prevention and/or treatment of CD22-positive B cell lymphomas or B cell leukemias whereby CD22 positivity applies to both cell surface and intracytoplasmic expression of the antigen.

B-cell derived neoplasms are still among the major causes of death in the western world. Around 1.500-2-000 new cases of high-grade B-cell lymphoma are expected yearly in Germany. Up to 40% of these patients will relapse after initial standard therapy or will not respond in the first place, suggesting the urgent need for alternative treatment options. Lymphoma incidence steeply increases with age, and for many patients aged 75 or more the prognosis is much worse. Around 75% of cases of Acute Lymphoblastic Leukemia (ALL) are derived from transformed B lymphocytes (B-lineage ALL). Around 1.000 individuals with B-lineage ALL are expected yearly in Germany. While children with ALL are frequently cured, older people with ALL (the disease has a second incidence peak at around 80 y. of age) are difficult to treat, both because of biological aggressiveness of the disease in aged individuals and frequent comorbidity and frailty. Chemotherapy is still the main treatment option for majority of cancer types despite its limitations regarding toxicity and resistance development. Even high-dose chemotherapy with stem cell rescue can salvage less than a third of patients with relapsed/refractory disease after first line therapy. Patients with relapsed or primarily refractory diffuse large B-cell lymphoma not suitable for high dose chemotherapy failing a salvage therapy hardly have any option for cure, and the disease is normally fatal within a few months.

Antibodies (humanized naked antibodies or different immunoconjugates) or chimeric antigen receptors (CARs) targeting B-cell lineage-specific cell surface proteins, e.g., CD19, CD20 or CD22 have been used to eliminate malignant B lymphocytes at the price of depleting also normal B cells.

CARs are chimeras of the antigen-binding domains of antibodies capable of recognizing cell surface antigens combined with TCR domains. T cells engineered to express the CAR thus target cells expressing the antigen to which the CAR binds, irrespective of any HLA restriction.

For example, CAR T cells targeting CD19 have proven successful in around 50% of relapsed diffuse large B-cell lymphoma (DLBCL) patients, demonstrating the potency of adoptive T cell therapy. Recently, clinical studies of adoptive T cell therapy (ATT) using chimeric antigenic receptor gene-transfer against the B cell antigen CD19 has achieved remarkable success and has been designated as "breakthrough cancer therapy". Several groups are developing this same strategy, mainly by targeting B cell lineage antigens such as CD19, CD20 and CD22.

CD22, also named B lymphocyte cell adhesion molecule or BL-CAM, is a validated target antigen strongly expressed on normal and neoplastic B cells. The antigen was long considered to be strictly lineage-specific, recently a weak expression on in vitro differentiated macrophages and dendritic cells was reported (Jahn et al. 2016 Oncotargets 7:71536-71546). For example, monoclonal anti-CD22 antibodies such as epratuzumab (Dörner et al., 2015, Autoimmun Rev. 14 (12): 1079-86), bi-specific antibodies such as Bs20x22 (Tuscano et al. 2011, Cancer Immunol. Immunother. 60:771-80), Immunotoxins such as Inotuzumab Ozogamicin (Dang N H et al. 2018, Br J Haemtol. 182:583-586) or CD22-specific CARs have been published and clinically tested (WO2012079000A1, WO2013059593A1, WO2014011518A1). CD22-specific CARs have been successfully used in a first clinical trial (Fry et al., 2018, Nat. Med. 24:20-28). However, tumor escape by down-regulation of surface expression of the target antigen is a major limitation of all antibodies—based strategies including CARs, leading to relapse in at least 50% of treated patients-despite the high costs. An attractive alternative is to target antigenic epitopes via the T cell receptor, which recognizes peptides presented in the context of MHC class I molecules: intracytoplasmatic expression of said antigens is retained in most cases even if surface expression is downregulated or even completely lost.

A TCR is a heterodimeric cell surface protein of the immunoglobulin super-family which is associated with invariant proteins of the CD3 complex involved in mediating signal transduction. TCRs exist in aß and yo forms, which are structurally similar, but have quite distinct anatomical locations and probably functions. The alpha and beta chains of native heterodimeric aßTCR are transmembrane proteins, which each comprises of two extracellular domains, a membrane-proximal constant domain, and a membrane-distal variable domain. Each of the constant and variable domains include an intra-chain disulfide bond. The variable domains contain the highly polymorphic loops that confer recognition specificity analogous to the complementarity determining regions (CDRs) of antibodies.

The variable region of each TCR chain comprises variable and joining segments, and in the case of the beta chain also a diversity segment. Each variable region comprises three CDRs (Complementarity Determining Regions) embedded in a framework sequence, one being the hypervariable region named CDR3. There are several types of alpha chain variable (Va) regions and several types of beta chain variable (VB) regions distinguished by their framework, CDR1 and CDR2 sequences, and by a partly defined CDR3 sequence. Unique "TRAV" or "TRBV" numbers are given to Va or VBs by IMGT (the international ImMunoGeneTics information system) nomenclature. T cell receptor specificity for the antigenic epitope is mainly determined by the CDR3 regions (Danska et al., 1990. J. Exp. Med. 172:27-33; Garcia et al., 2005. Cell 122 (3): 333-336).

The use of TCR gene therapy allows equipping patients' own T cells with desired specificities and generation of a large number of T cells in a short period of time, avoiding their exhaustion. The TCR may be transduced into central memory T cells or T cells with stem cell-like characteristics (Tscm), which may ensure better persistence and function upon transfer. TCR-engineered T cells may be infused into cancer patients that have, e.g., been rendered lymphopenic by chemotherapy or irradiation, facilitating homeostatic T cell proliferation and inhibiting immune-mediated rejection.

A TCR targeting a CD22-epitope has been published in 2016 by Jahn et al. (Oncotargets 7:71536-71546). This TCR has been isolated from HLA-B7-negative individuals with an HLA-B7 tetramer bound with a CD22 peptide. Because of this strategy, only individuals with the HLA-B7 MHC haplotype, around 15-20% of the population, are suitable for therapy with this TCR.

In view of this, the present inventors addressed the problem of providing an advantageous TCR construct capable of specifically targeting a CD22 epitope which is suitable for treatment of a higher percentage of the patients with B cell lymphoma or B cell leukemia. This problem is solved by the subject matter of the claims.

The inventors provide TCR constructs recognizing epitopes of CD22 in the context of HLAA*-02, an MHC haplotype expressed in about 45% of the Caucasian/West European population. In particular, preferred TCR constructs provided by the invention recognizes the peptide of SEQ ID NO: 1 in the context of HLA-A*02, wherein the TCR alpha chain construct comprises a CDR3 sequence of SEQ ID NO: 4, and/or wherein the TCR beta chain construct comprises a CDR3 sequence of SEQ ID NO: 22. Other TCR constructs provided by the invention recognizes the peptide of SEQ ID NO: 1 in the context of HLA-A*02, wherein the TCR alpha chain construct comprises a CDR3 sequence of SEQ ID NO: 4, and/or wherein the TCR beta chain construct comprises a CDR3 sequence of SEQ ID NO: 7.

In the context of the invention, HLA-A*02 means any of HLA-A*02:01, HLA-A*02:04, 05, 07, 10, and possibly other subtypes of HLA-A*02 but not HLA-A*02:02 and 08. As the affinity and specificity may be further optimized by methods known in the art, as described in more detail below, the invention also provides a nucleic acid encoding at least one TCR alpha or beta chain construct of a TCR construct capable of specifically binding to the peptide of SEQ ID NO: 1 in the context of HLA-A*02, a) wherein the TCR alpha chain construct comprises a CDR3 sequence having an amino acid (aa-) sequence identity of at least 83%, preferably, at least 90% to SEQ ID NO: 4, and/or wherein the TCR beta chain construct comprises a CDR3 sequence having a sequence identity of at least 83%, preferably, at least 90% to SEQ ID NO: 22 or of at least 83%, preferably, at least 90% to SEQ ID NO: 7.

Thus, the inventors provide two distinct, but highly similar TCR beta chain constructs which both pair with the same TCR alpha chain construct, and form TCR constructs that specifically recognize the peptide of SEQ ID NO: 1, preferably, they do not have significant cross-reactivity to non-CD22 self-peptides. The TCR beta chain constructs of the invention differ from each other only in two amino acids of CDR3.

Advantageously, the inventors could show that the TCR constructs of the invention have a high functional avidity as indicated by recognition and killing of target cells expressing different levels of CD22, including patient derived CD22 expressing tumor cells or tumor cell lines (cf. examples). Preferred TCR constructs of the invention have a $K_d$ value of about $5*10^{-8}$, preferably, $1.1 \times 10^{-8}$ or better. The $K_d$ value can be determined by peptide titration on T2 cells, as disclosed in the experimental part. The T cells expressing a TCR construct of the invention were also able to significantly reduce tumor growth and extend survival in a pre-ALL xenograft mouse model.

In a first embodiment, in the nucleic acids of the invention, the encoded TCR alpha chain construct comprises 1) a CDR1 sequence having a sequence identity of at least 83%, preferably, at least 90% to SEQ ID NO: 2, 2) a CDR2 sequence having a sequence identity of at least 83%, preferably, at least 90% to SEQ ID NO: 3,
3) and a CDR3 sequence having a sequence identity of at least 83%, preferably, at least 90% to SEQ ID NO: 4, and/or the TCR beta chain construct comprises a
4) CDR1 sequence having a sequence identity of at least 83%, preferably, at least 90% to SEQ ID NO: 5,
5) a CDR2 sequence having a sequence identity of at least 83%, preferably, at least 90% to SEQ ID NO: 6,
6) and a CDR3 sequence having a sequence identity of at least 83%, preferably, at least 90% to SEQ ID NO: 7.

Preferably, all amino acid identities are at least 90% to the respective CDRs.

Preferably, in the nucleic acids of the invention, the encoded TCR alpha chain construct comprises a CDR1 sequence having a sequence identity of at least 90% to SEQ ID NO: 2, a CDR2 sequence having a sequence identity of at least 90% to SEQ ID NO: 3, and a CDR3 sequence of SEQ ID NO: 4 and/or the TCR beta chain construct comprises a CDR1 sequence having a sequence identity of at least 90% to SEQ ID NO: 5, a CDR2 sequence having a sequence identity of at least 90% to SEQ ID NO: 6 and a CDR3 sequence of SEQ ID NO: 7.

Optionally, in the nucleic acids of the invention, the encoded TCR alpha chain construct comprises a CDR1 sequence having a sequence identity of at least 95% to SEQ ID NO: 2, a CDR2 sequence having a sequence identity of at least 95% to SEQ ID NO: 3 and a CDR3 sequence of SEQ ID NO: 4 and/or the TCR beta chain construct comprises a CDR1 sequence having a sequence identity of at least 95% to SEQ ID NO: 5, a CDR2 sequence having a sequence identity of at least 95% to SEQ ID NO: 6 and a CDR3 sequence of SEQ ID NO: 7.

Preferably, in the nucleic acids of the invention, the encoded TCR alpha chain construct comprises a CDR1 sequence of SEQ ID NO: 2, a CDR2 sequence of SEQ ID NO: 3 and a CDR3 sequence of SEQ ID NO: 4 and/or the TCR beta chain construct comprises a CDR1 sequence of SEQ ID NO: 5, a CDR2 sequence of SEQ ID NO: 6 and a CDR3 sequence of SEQ ID NO: 7.

In the nucleic acids of the invention, the encoded TCR alpha chain construct may comprise a variable region having a sequence identity of at least 90% to SEQ ID NO: 16 (without the leader sequence, i.e., without aa 1-20), and/or the TCR beta chain construct may comprise a variable region having a sequence identity of at least 90% to SEQ ID NO: 19 (without aa 1-25). The leader sequence is from aa 12-25. The TCR chain typically does not comprise the leader sequence. In the experiments, TCR with this sequence are designated CD22 TCR.

Optionally, in the nucleic acids of the invention, the TCR alpha chain construct comprises a variable region having a sequence identity of at least 95% to SEQ ID NO: 16 (without the leader sequence, i.e., without aa 1-20), and/or the TCR beta chain construct comprises a variable region having a sequence identity of at least 95% to SEQ ID NO: 19 (without aa 1-25). Preferably, in such nucleic acids, the sequence identity to the defined CDR1, CDR2 and CDR3 regions is 100%.

Preferably, in the nucleic acids of the invention, the encoded TCR alpha chain construct comprises a variable region of NO: 16 (without the leader sequence, i.e., without aa 1-20), and/or the TCR beta chain construct comprises a variable region of SEQ ID NO: 19 (without aa 1-25).

The variable region of TCR alpha chain may be encoded by SEQ ID NO: 14 or, preferably, SEQ ID NO: 15 (codon-optimized). The variable region of TCR beta chain may be encoded by SEQ ID NO: 17 or, preferably, SEQ ID NO: 18 (codon-optimized).

The inventors have identified a further TCR construct of the invention, which is designated CD22 TCR 3225. Of note, the alpha chain construct is the same as fond in the first TCR construct. The beta chain construct comprises a CDR3 sequence having a sequence identity of at least 83% to SEQ ID NO: 7, i.e., it can be considered an optimized variant of the beta chain construct of the first TCR construct. Preferred beta chain constructs of the second TCR construct are, except for two amino acids difference in the CDR3, identical to preferred beta chain constructs of the first TCR construct.

Thus, in a second, preferred embodiment, in the nucleic acids of the invention, the encoded TCR alpha chain construct comprises
1) a CDR1 sequence having a sequence identity of at least 83%, preferably, at least 90% to SEQ ID NO: 2,
2) a CDR2 sequence having a sequence identity of at least 83%, preferably, at least 90% to SEQ ID NO: 3,
3) and a CDR3 sequence having a sequence identity of at least 83%, preferably, at least 90% to SEQ ID NO: 4, and/or the TCR beta chain construct comprises a
4) CDR1 sequence having a sequence identity of at least 83%, preferably, at least 90% to SEQ ID NO: 20,
5) a CDR2 sequence having a sequence identity of at least 83%, preferably, at least 90% to SEQ ID NO: 21,
6) and a CDR3 sequence having a sequence identity of at least 83%, preferably, at least 90% to SEQ ID NO: 22.

The comparison of the first and second TCR constructs of the invention, which differ in 2 amino acids in the CDR3 region of the beta chain construct, shows that the sequence of the CDRs, e.g., of the CDR3, can be varied by up to two amino acids while maintaining or even increasing the affinity to the target epitope. Optionally, the two amino acids differing between the CDR3 of the first and the second TCR beta chain construct, i.e., positions 5 and/or 6 or the CDR3 sequences, are mutated, preferably, substituted by other amino acids such as conservative substitutions (e.g., negatively charged amino acids E and D can be substituted for each other, or positively charged amino acids R, H and L can be substituted for each other, or amino acids with polar side chains S, T, N or Q can be substituted for each other (preferably, S and T can be substituted for each other, or N and Q can be substituted for each other), or amino acids with hydrophobic side chains G, A, I, L, M, F, W, Y, V can be substituted for each other, or amino acids with aromatic side chains can be substituted for each other, or amino acids with hydrophobic non-aromatic side chains can be substituted for each other).

For example, position 5 of the CDR3 can be selected from the group comprising P, E and D, preferably, E and D, most preferably, E.

Position 6 can be selected from the group comprising A, G, I, L, M, F, W, Y, V, S, T, N or Q, preferably, A, V, I and L, most preferably, A.

The invention thus also provides a beta chain construct, and a TCR construct comprising the same, wherein positions 5 and 6 of the CDR3 are PA or ES, wherein the other positions in the CDR3 correspond to SEQ Id NO: 7 and 22.

Preferably, all amino acid identities are at least 90% to the respective CDRs.

Preferably, in the nucleic acids of the invention, the encoded TCR alpha chain construct comprises a CDR1 sequence having a sequence identity of at least 90% to SEQ ID NO: 2, a CDR2 sequence having a sequence identity of at least 90% to SEQ ID NO: 3, and a CDR3 sequence of SEQ ID NO: 4 and/or the TCR beta chain construct comprises a CDR1 sequence having a sequence identity of at least 90% to SEQ ID NO: 20, a CDR2 sequence having a sequence identity of at least 90% to SEQ ID NO: 21 and a CDR3 sequence of SEQ ID NO: 23.

Optionally, in the nucleic acids of the invention, the encoded TCR alpha chain construct comprises a CDR1 sequence having a sequence identity of at least 95% to SEQ ID NO: 2, a CDR2 sequence having a sequence identity of at least 95% to SEQ ID NO: 3 and a CDR3 sequence of SEQ ID NO: 4 and/or the TCR beta chain construct comprises a CDR1 sequence having a sequence identity of at least 95% to SEQ ID NO: 20, a CDR2 sequence having a sequence identity of at least 95% to SEQ ID NO: 21 and a CDR3 sequence of SEQ ID NO: 22.

Preferably, in the nucleic acids of the invention, the encoded TCR alpha chain construct comprises a CDR1 sequence of SEQ ID NO: 2, a CDR2 sequence of SEQ ID NO: 3 and a CDR3 sequence of SEQ ID NO: 4 and/or the TCR beta chain construct comprises a CDR1 sequence of SEQ ID NO: 5, a CDR2 sequence of SEQ ID NO: 6 and a CDR3 sequence of SEQ ID NO: 7.

In the nucleic acids of the invention, the encoded TCR alpha chain construct may comprise a variable region having a sequence identity of at least 90% to SEQ ID NO: 16 (without the leader sequence, i.e., without aa 1-20), and/or the TCR beta chain construct may comprise a variable region having a sequence identity of at least 90% to SEQ ID NO: 25 (without the leader sequence, i.e., without aa 1-14). Optionally, in the nucleic acids of the invention, the TCR alpha chain construct comprises a variable region having a sequence identity of at least 95% to SEQ ID NO: 16 (without the leader sequence, i.e., without aa 1-20), and/or the TCR beta chain construct comprises a variable region having a sequence identity of at least 95% to SEQ ID NO: 25 (without the leader sequence, i.e., without aa 1-14). Preferably, in such nucleic acids, the sequence identity to the defined CDR1, CDR2 and CDR3 regions is 100%.

Preferably, in the nucleic acids of the invention, the encoded TCR alpha chain construct comprises a variable region of NO: 16 (without the leader sequence, i.e., without aa 1-20), and/or the TCR beta chain construct comprises a variable region of SEQ ID NO: 25 (without the leader sequence, i.e., without aa 1-14).

The beta chain construct may comprise human TRBV20-1*01-TRBJ2-1*01-TRBD2*02 F.

The variable region of TCR alpha chain construct may be encoded by SEQ ID NO: 14 or, preferably, SEQ ID NO: 15 (codon-optimized). The variable region of TCR beta chain construct may be encoded by SEQ ID NO: 17 or, preferably, SEQ ID NO: 18 (codon-optimized). The CDR3 region of the TCR beta chain construct may be encoded by SEQ ID NO: 26 or, preferably, SEQ ID NO: 27 (codon-optimized).

Preferably, a nucleic acid of the invention encodes one TCR alpha chain construct and one TCR beta chain construct. In the context of the present invention, "a" is understood to mean "one or more" unless expressly stated otherwise. Accordingly, for example, as the TCR construct of the invention contains both alpha and beta chain constructs, it may be encoded by either one or two nucleic acids. The alpha and beta chain constructs together are capable of specifically binding to the peptide of SEQ ID NO: 1 in complex with HLA-A*02. As intermediate products, the alpha and beta chain constructs and the nucleic acids encoding them are also subject matter of the invention by themselves.

Preferably, in all TCR alpha and/or beta chain constructs of the invention, the sequence identity to the CDR regions defined herein is 100%.

TABLE 1

CDRs of preferred TCRs

| | Alpha chain (SEQ ID NO:) | Beta chain (SEQ ID NO:) |
|---|---|---|
| CD22 TCR | | |
| CDR1 | VTNFRS (2) | DFQATT (5) |
| CDR2 | LTSSGIE (3) | SNEGSKA (6) |
| CDR3 | CAVDNQGGKLIF (4) | CSARPSGVYNEQFF (7) |
| CD22 TCR 3225 | | |
| CDR1 | VTNFRS (2) | DFQATT (20) |
| CDR2 | LTSSGIE (3) | SNEGSKA (21) |
| CDR3 | CAVDNQGGKLIF (4) | CSAREAGVYNEQFF (22) |

However, based on the defined CDR3 and variable region sequences provided by the invention, it is possible to carry out affinity maturation of the TCR sequences (Chervin et al. 2008. J Immunol Methods. 339 (2): 175-84; Robbins et al., 2008. J Immunol. 180:6116). Nonsynonymous nucleotide substitutions, which lead to amino acid exchanges in the CDR3 sequence, may lead to enhanced affinity of the TCR to target antigen. Furthermore, TCR sequence changes in other parts of the variable TRA and TRB regions may change affinity of the TCR to the peptide-MHC complex. This may increase overall affinity of the TCR to the peptide-MHC, but harbors the risk of unspecific recognition and increased cross-reactivity (Linette et al. 2013. Blood 122 (6): 863-72). It is crucial that TCRs varying from the specific sequences provided retain exclusive specificity for the target antigen provided, i.e., that they are not cross-reactive, most importantly, that they do not have cross-reactivity for human self-peptides. Potential cross-reactivity of TCR can be tested against known self-peptides loaded on cells with the correct MHC allele (Morgan et al., 2013, J. Immunother. 36, 133-151). Accordingly, it is important that adoptive transfer of T cells expressing the TCR construct of the invention has no or significant negative effects on healthy tissue.

A TCR alpha and/or beta chain construct of the invention may comprise all characteristics or domains corresponding to its native counterpart, but this is not essential. Preferably, the TCR alpha and/or beta chain construct comprises at least a variable region, or a variable and a constant region, e.g., the variable and/or constant region having at least 60%, at least 70%, at least 80%, at least 90% or at least 95% sequence identity to a human variable or constant TCR region. For adoptive TCR therapy, it is preferred that the TCR construct comprises full length TCR alpha and beta chains comprising variable, constant and transmembrane regions. The TCR construct preferably is of essentially human origin to minimize immunogenicity. It may also be completely human. Nucleic acids encoding the TCR alpha and beta chain construct may thus comprise SEQ ID NO: 10 and SEQ ID NO: 13, respectively (both human, codon-optimized). To prevent pairing with endogenous TCR chains, the constructs of the invention however preferably contain one or more, e.g., 1-5, 1-10 or 1-20, amino acid exchanges, insertions or deletions in comparison to a human sequence, e.g., providing an additional cysteine to enable formation of an additional disulfide bond (Kuball et al., 2007, Blood 106 (6), 2331-8). The constant regions of such TCR may be minimally murine constant regions, meaning that in TCR beta constant regions five amino acids and in TCR alpha constant region four amino acids are exchanged to murine counterparts as defined in Sommermeyer et al., 2010, J. Immunol. 184, 6223-31. Nucleic acids encoding the TCR alpha and beta chain construct may thus comprise SEQ ID NO: 9 and SEQ ID NO: 12, respectively (both minimally murine, codon-optimized). To this end, the constant region of the TCR alpha and beta chain construct may also be murine constant regions, e.g., encoded by SEQ ID NO: 8 and SEQ ID NO: 11, respectively (both codon-optimized).

Single chain constructs (scTCR) are encompassed as well as heterodimeric TCR constructs. A scTCR can comprise a variable region of a first TCR chain construct (e.g., an alpha chain) and an entire (full-length) second TCR chain (e.g., a beta chain), or vice versa. Furthermore, the scTCR can optionally comprise one or more linkers, which join the two or more polypeptides together. The linker can be, for instance, a peptide which joins together two single chains, as described herein. Also provided is such a scTCR of the invention, fused to a cytokine, e.g., a human cytokine, such as IL-2, IL-7 or IL-15.

The TCR construct according to the invention can also be provided in the form of a multimeric complex, comprising at least two scTCR molecules, wherein said scTCR molecules are each fused to at least one biotin moiety, and wherein said scTCRs are interconnected by biotin-streptavidin interaction to allow the formation of said multimeric complex. Also provided are multimeric complexes of a higher order, comprising more than two, e.g., four, scTCR of the invention.

The TCR construct of the invention can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and particles (e.g., gold particles or magnetic particles).

The nucleic acid of the invention, in particular if it encodes at least one TCR alpha and beta chain construct of the TCR construct, may be a viral vector, a transposon or a vector suitable for CRISPR/CAS based recombination, such as the self-inactivating lentiviral vector LentiCrisprV2-CD22 TCR expressing Cas9, CD22 TCR protein and a sgRNA or a plasmid suitable for in vitro RNA transcription such as pcDNA3.1 with T7 promotor, or any nucleic acid suitable for insertion into a host genome.

Preferably, the TCR alpha chain construct and/or TCR beta chain construct or TCR construct of the invention is a vector. Suitable vectors include those designed for propagation and expansion, or for expression or both, such as plasmids and viruses. The vector may be an expression vector suitable for expression in a host cell selected from the group comprising a human T cell or a human T cell precursor, preferably, a human T cell such as CD8+ T cell, e.g., a CD8+ central-memory T cell, CD8+ effector-memory T cell, CD8+ stem cell-like T cell. The vector may be a viral vector, e.g. a retroviral, in particular gamma-retroviral or lentiviral vector. Examples of suitable expression vectors include the retroviral vector MP71.

The expression vector comprises regulatory sequences, such as transcription and translation initiation and termination codons, which are specific to the type of host cell (for example, bacterium, fungus, plant, or animal cell, e.g., a human CD8+ T cell as defined above) into which the vector is to be introduced and in which the expression of the nucleic acid of the invention shall be performed. Furthermore, the vector of the invention may include one or more marker genes, which allow for selection of transformed or transfected hosts. The expression vector can comprise a native or, preferably, heterologous promotor operably linked to the nucleotide sequence encoding the construct of the invention, or to the nucleotide sequence which is complementary to or which hybridizes to the nucleotide sequence encoding the constructs of the invention. The selection of promotors includes, e.g., strong, weak, inducible, tissue-specific and developmental-specific promotors. The promotor can be a nonviral promotor or a viral promotor. Preferably, it is a heterologous promotor, i.e., a promotor not naturally linked to TCR in human T cells, such as long terminal repeat promoter, which is suitable for expression in human T cells. The inventive expression vectors can be designed for either transient expression, for stable expression, or for both. Also, the expression vectors can be made for constitutive expression or for inducible expression. The vector may also allow for in vitro transcription of RNA. The nucleic acid of the invention, preferably, an expression vector suitable for expression of the TCR construct of the invention in human CD8+ T cells may, as a safety tag, further encode a cell surface protein typically expressed by B cells but not to a significant extent in native human T cells, e.g. CD20 or a truncated receptor such as a truncated Epithelial growth factor (EGF-) receptor under the control of a promotor suitable for expression of the cell surface protein in said T cell. In case the patient has any problems, e.g., with autoimmunity after therapy with a nucleic acid, protein or host cell of the invention, the patient may then be treated with a therapeutic agent targeting the safety tag, e.g., CD20, or anti-EGFR antibody which will eliminate the host cells of the invention. Suitable safety tags have also been described by Philip et al., 2014, Blood 124 (8), 1277-87; Paszkiewicz et al., 2016, JCI 126 (11), 4262-72; Wang et al., 2011, Blood 118 (5), 1255-1263.

The present invention also provides a protein, i.e., an alpha or beta chain construct, or, preferably, a TCR receptor construct comprising both alpha and beta chain constructs, which is capable of specifically binding HLA-A*02 in combination with the epitope of SEQ ID NO: 1. The protein is preferably encoded by the nucleic acids of the invention. It is preferably expressed as a transmembrane protein by a host cell. A TCR alpha and/or beta chain construct of a TCR construct capable of specifically binding to a peptide of SEQ ID NO: 1 in the context of HLA-A*02, wherein the TCR alpha chain construct comprises a CDR3 sequence having a sequence identity of at least 83% to SEQ ID NO: 4, and/or wherein the TCR beta chain construct comprises a CDR3 sequence having a sequence identity of at least 83% to SEQ ID NO: 22 is preferred.

The invention also provides a host cell comprising a nucleic acid or protein of the invention. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell or T cell precursor, in particular, a human T cell. The T cell can be any T cell, such as a cultured T cell, e.g. a primary T cell, or a T cell from a cultured T cell line, or a T cell obtained from a mammal, preferably, it is a T cell or T cell precursor from a human patient. The T cell can be obtained from numerous sources, such as blood, bone marrow, lymph node, the thymus, or other tissues or fluids. T cells can also be enriched for or purified. Preferably, the T cell is a human T cell. More preferably, the T cell is a T cell isolated from a human, e.g., a human patient or a donor in case of allogeneic transplanted patients. The T cell can be any type of T cell, but it preferably is a CD8+ cell. It can be of any developmental stage, including but not limited to tumor infiltrating cells (TILs), effector cells, central effector cells, memory T cells, naive T cells, and the like, preferably central-memory T cells.

The host cell of the invention preferably comprises a nucleic acid of the invention and/or a protein of the invention, wherein the host cell preferably is a CD8+ T cell, optionally, a human CD8+ T cell. The nucleic acid in this case typically is an expression vector suitable for constitutive expression of alpha and beta chain constructs of the invention in the human CD8+ T cell.

The invention thus provides a human CD8+ T cell comprising a nucleic acid encoding a TCR alpha and/or beta chain construct of a TCR construct capable of specifically binding to a peptide of SEQ ID NO: 1 in the context of HLA-A*02, wherein the TCR alpha chain construct comprises a CDR3 sequence having a sequence identity of at least 83% to SEQ ID NO: 4, and/or wherein the TCR beta chain construct comprises a CDR3 sequence having a sequence identity of at least 83% to SEQ ID NO: 22 is preferred. Both alpha and beta chain together can specifically recognize a CD22 epitope in the context of HLA-A2.

The invention also provides a pharmaceutical composition comprising
a) a nucleic acid of the invention encoding a TCR construct capable of specifically binding to a peptide of SEQ ID NO: 1 in the context of HLA-A*02 (as specified above);
or
b) a protein of the invention comprising a TCR construct capable of specifically binding to a peptide of SEQ ID NO: 1 in the context of HLA-A*02 (as specified above); or
c) a host cell of the invention expressing a TCR construct capable of specifically binding to a peptide of SEQ ID NO: 1 in the context of HLA-A*02 (as specified above).

Preferably, the pharmaceutical composition comprises a human CD8+ host cell of the invention, as defined herein. Said host cell may, e.g., comprise a vector encoding a TCR construct comprising a TCR alpha chain construct and a TCR beta chain construct capable of specifically recognizing the peptide of SEQ ID NO: 1 in the context of HLA-A*02. Preferably, the vector is an expression vector for expression of both alpha and beta chain constructs on one nucleic acid, e.g., separated by a p2A element. The variable regions of the TCR chains as defined herein are linked with constant regions, preferably, with minimally murine constant regions.

Alternatively, the patient may also be administered a nucleic acid of the invention, in particularly, an expression vector, for in vivo transduction of T cells.

The pharmaceutical composition may also be part of a kit comprising further therapeutics, e.g., an antibody such as rituximab, or a CAR, which is preferably expressed by a CD8+ T cell, typically a different CD8+ T cell to the T cell expressing the TCR construct of the present invention, wherein the CAR may target a B cell lineage antigen (for example CD19, CD20 or CD22), preferably, a CAR capable of targeting CD19, or a chemotherapeutic agent, e.g., high dose chemotherapy, or a T cell expressing a TCR construct capable of targeting another antigen expressed by tumor cells, e.g., MyD88 L265P or immunotherapeutic drugs such as immune checkpoint inhibitors (e.g. CTLA-4, PD1, PDL1 blocking antibodies). Most likely such TCR combined with CAR or other TCR would be administered in one dosage form, and thus, e.g, comprised in one pharmaceutical composition. The pharmaceutical composition may be for use in combination with any of the above further therapeutics, wherein the further therapeutic is to be administered simultaneously, e.g., in the same or a different composition, or in different compositions within a short time span, e.g., within one day, two days or a week.

The pharmaceutical composition of the invention or the kit of the invention may be for use in the prevention and/or treatment of a disease associated with abnormal proliferation and/or activation of a B cell or a B cell precursor, in particular in a patient having a B cell lymphoma or a B cell leukemia. In a preferred embodiment, the tumor cells have been confirmed to express HLA-A*02. They further express CD22, with or without cell surface expression (as detected by FACS-staining or immunohistology). Preferably, the disease is treated.

The patient may have a non-Hodgkin lymphoma of B-cell lineage, including low-grade B-cell lymphomas such as follicular lymphoma, mantle cell lymphoma, immunocytic lymphoma, Waldenstrøem Macroglobulinemia, or "high-grade" lymphomas such as Burkitt lymphoma or diffuse large B-cell lymphoma (DLBCL) in all its variants, including Activated type B-cell lymphoma, Germinal Center type B-cell lymphoma, unclassified B-cell lymphoma, Primary mediastinal B-cell lymphoma, primary CNS lymphoma, cutaneous DLBCL, leg-type DLBCL or testicular DLBCL as well as post-transplant lymphoproliferative disorders (PTLDs). All leukemias of B-cell lineage are also suitable for treatment, including acute lymphoblastic leukemia of B-cell type (B-ALL), such as pre-ALL, chronic lymphocytic leukemia (B-CLL), prolymphocytic leukemia (PLL) of B-cell type, and hairy cell leukemia.

Preferably, the disease has been treated and relapsed after one or more lines of therapy or be refractory to primary treatment. The present invention also provides a method for treating a subject suffering from a disease as specified above, in particular, a tumor or tumor disease as described herein, comprising administering a nucleic acid, protein or host cell of the invention. Preferably the subject is a subject in need of such a treatment, i.e. a patient. The subject in preferred embodiments is a mammalian subject, preferably a human patient, suffering from a tumor or tumor disease. The active agent is administered in an effective amount.

The preferred medicinal use of the invention relates to immune therapy, in particular adoptive T cell therapy. The product and methods of the invention are used in the context of adoptive T cell therapy. The administration of the compounds of the invention can for example involve the administration, e.g., infusion of T cells of the invention into said patient. Preferably such T cells are autologous T cells of the patient which were in vitro transduced with a nucleic acid of the present invention. Preferably, the patient expresses HLA-A*02, such as HLA-A*02:01 or HLA-A*02:04, 05, 07, or 10.

The host cells may express HLA-A2 themselves, e.g., that is normally the case with autologous T cells that have only been modified to express the TCR construct of the invention. However, that is not required. The host T cells of the invention may also be T cells that do not express HLA-A2, e.g., in the context of allogeneic or mismatched (haploidentical) T cell therapy or in the form of autologous T cells genetically modified not to express HLA-A2, e.g., through HLA-A2 knockout by means of CRISPR/Cas or knockdown with suitable inhibitory nucleic acids such as but not limited to siRNA/miRNA molecules. For example, T cells modified not to express any HLA can be used as host cells, which are suitable for use in any patient without provoking an immune response.

The treatment of the invention may be first-line treatment of the patient. Preferably the treatment of the invention is second or later-line treatment of the patient, e.g., if the patient has relapsed or is refractory to therapy with one or more alternative agents (e.g., chemotherapy including chemoimmunotherapy as defined by the combination of a chemotherapy regimen and administration of a B-cell specific monoclonal antibody or CAR-based therapy, for example against a B cell lineage antigen such as CD19, CD20 or CD22). Preferably, the patient has relapsed or primarily refractory B cell lymphoma or leukemia as indicated above not suitable for further chemotherapy, including autologous or allogeneic stem cell transplantation.

The invention also relates to a method of preparing a host cell of the invention, comprising introducing an expression vector encoding a TCR construct of the invention into a suitable host cell, preferably, a human CD8+ T cell isolated from a patient. Said host cell can then be reintroduced into the patient The present invention is further illustrated in the following examples with reference to the accompanying figures and sequences, nevertheless, without being limited thereto. For the purposes of the present invention, all references as cited herein are incorporated by reference in their entirety.

FIGURE LEGENDS

FIG. 1. Isolation and characterization of CD22 TCR a) Human TCR loci-transgenic mice (hTCR loci-tg) (Li et al., 2010, Nat. Med. 16, 1029-35) were vaccinated with DNA-coated gold particles by gene gun. One week after vaccination, reactivity towards CD22 was tested in blood T cells and spleen cells by cocultivation with NIH3T3+ HHD cells engineered to express CD22 (+CD22) or untransduced NIH3T3+ HHD cells (untransd.). Reactivity was analysed by intracellular IFNγ staining (left panel). Next, splenocytes were tested for 12 hours with a peptide-library and in silico predicted peptides to identify epitope specificity for the FLSNDTVQL peptide (also designated FLS-peptide, SEQ ID NO: 1). Only the coculture with specific peptide (+ FLS peptide) or without peptide (negative control) is shown in intracellular IFNγ staining (upper right panel). T cells were enriched with the corresponding peptide for 10 days in vitro. The FLS peptide has been previously described. Its IC50 was determined to be 11 nM with NetMHC3.4 (http://www.cbs.dtu.dk/services/NetMHC-3.4/). On day 10, cell were restimulated with FLS peptide for four hours and IFNγ-positive cells were FACS-sorted after IFNγ capture assay. As negative control, cells were not incubated with IFN capture antibody (negative control) (lower right panel). From sorted cells, RNA was isolated and, by means of RACE PCR, the TCR sequences were identified. b) The TCR was cloned into a γ-retroviral vector in the configuration of TCRβ-p2a-TCRα linked by a viral peptide linker (p2a). The whole sequence is codon-optimized. The TCR constant regions are derived from mouse (mTRBC, mTRAC) but can also be derived from human or with few amino acids derived from the murine sequence (minimal murinized). c) Retroviral transduction of human T cells with the γ-retroviral vector MP71 expressing the CD22 TCR. Cells are stained for human CD8 and murine TCRB constant region. d) TCR-transduced T cells were incubated with peptide-loaded T2 cells for peptide titration. After 18-20 hours, IFNγ was detected in the cell supernatant by ELISA. The amount of IFNγ with 10 UM peptide-loaded T2 cells was set as 100%. $K_d$ value was calculated with 50% of maximal IFNγ release. The curves and data points are derived from 4 experiments with 4 individual T cell donors.

Figure 2:
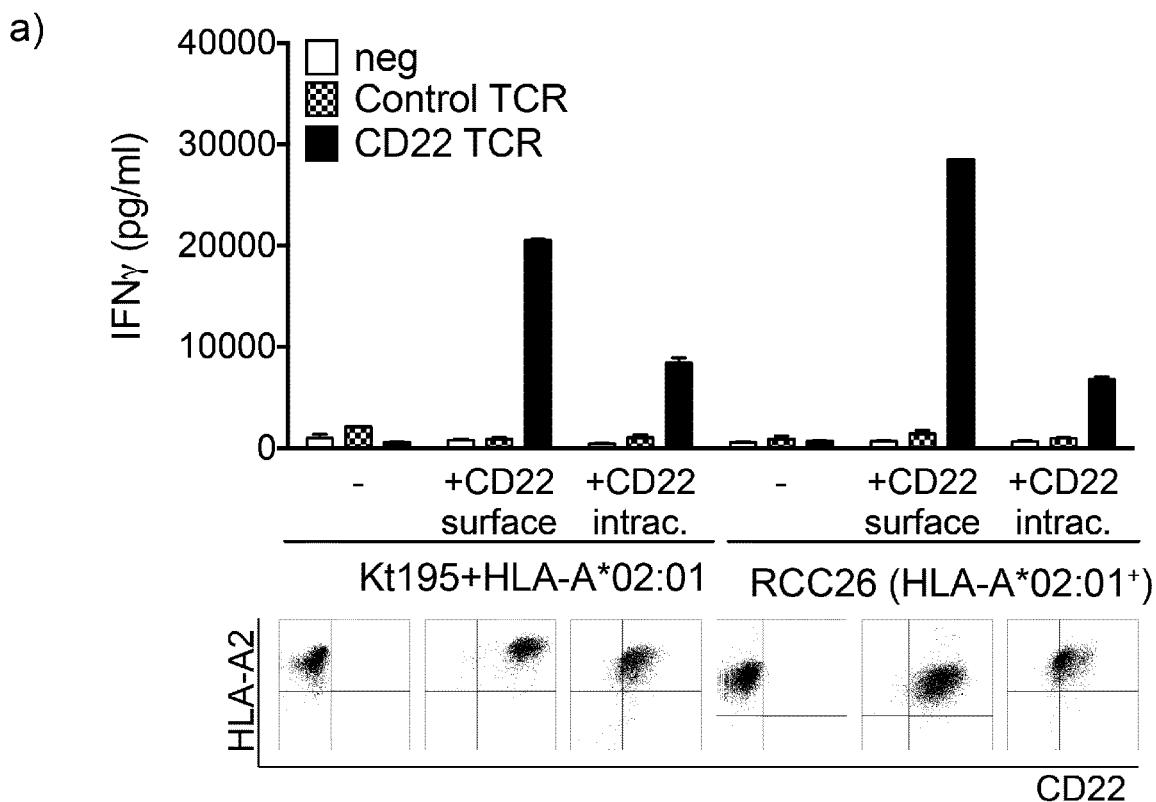
Figure 2:
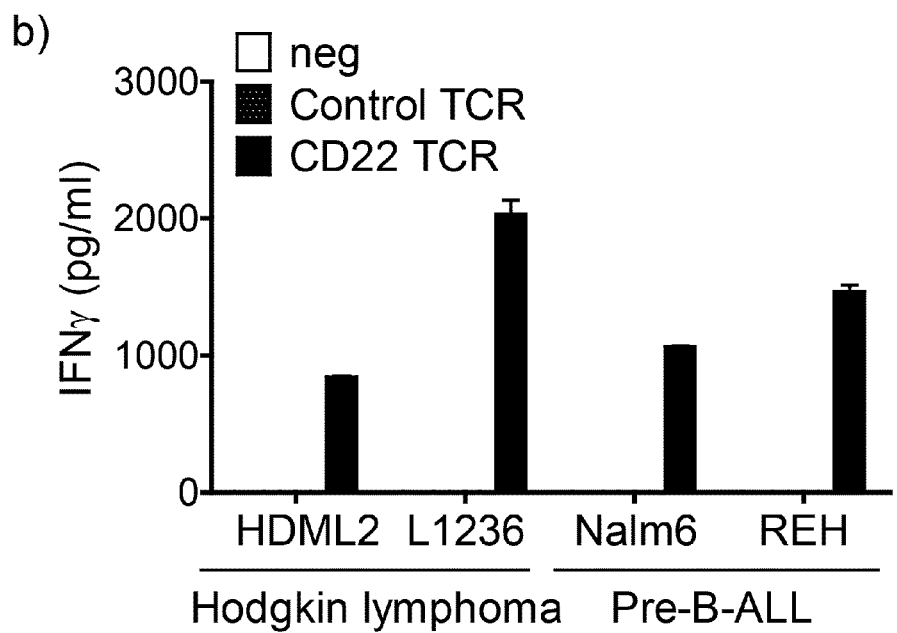
Figure 2:
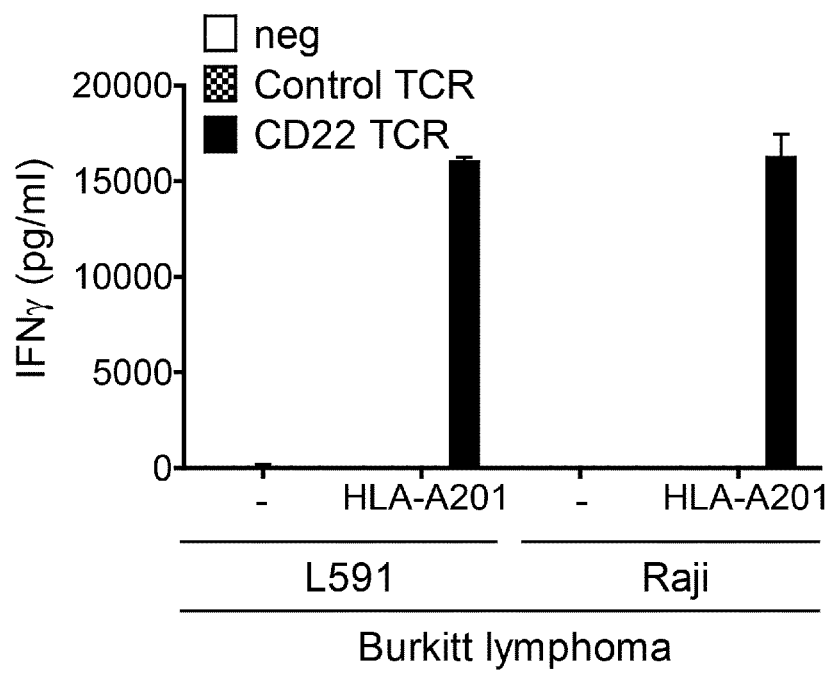
Figure 2:
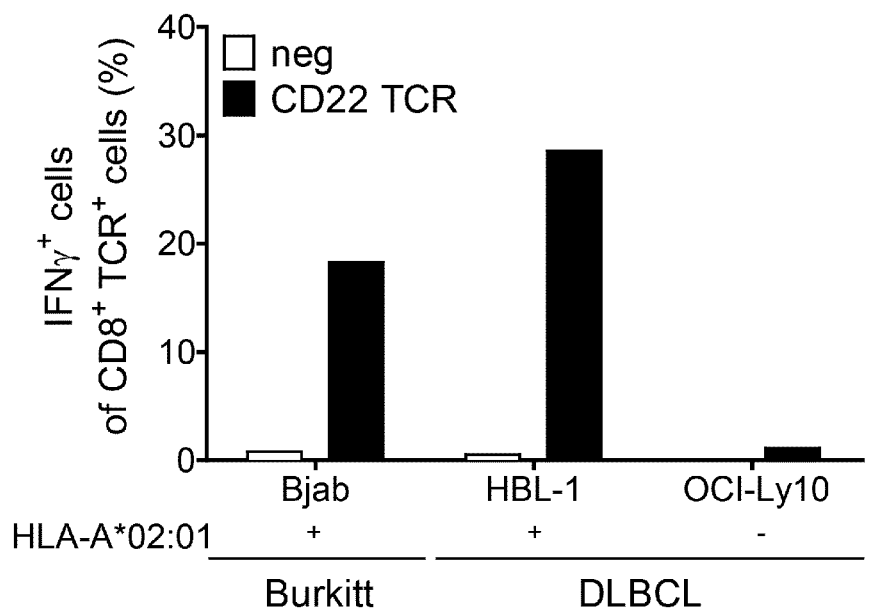

FIG. 2. The CD22 TCR recognizes a) CD22 gene-modified HLA-A*02:01-positive renal cell carcinoma cell lines and b) different types of Hodgkin lymphoma and Pre-B-ALL that express CD22 and HLA-A*02 or c) Burkitt lymphoma cell lines that were genetically modified for HLA-A*02:01 expression as well as d) diffuse large B cell lymphoma (DLBCL) lines. a-d) Human peripheral blood lymphocytes (hPBLs) were retrovirally transduced with the CD22 TCR (black bar) or control TCR (black dotted bar) or were kept untransduced (neg; white bar) and were tested in a cocultivation assay with target cells. a-c) After 18-20 hours, IFNγ was detected in the cell supernatant by ELISA. The shown data is representative for at least three PBL donors. a) Renal cell carcinoma cell lines Kt195+ HLA-A*02:01 and RCC26 were gene-modified with a full-length CD22 or a truncated CD22 without the intracellular and transmembrane part, leading to intracellular expression of truncated CD22 still comprising the epitope (+CD22intrac.). FACS dot plots below show the expression profile of the target cells Kt195+ HLA-A*02:01 and RCC26, either untransduced or CD22 transduced. Cell staining was done with anti-CD22 (clone IS7, Biozol) antibody and anti-HLA-A2 antibody (clone BB7.2, BD). Cells with CD22intrac. were intracellularly stained for CD22. c) The Burkitt lymphoma cell lines L591 and Raji were retrovirally transduced to obtain HLA-A*02:01 expression. d) After cocultivation with DLBCL lines HBL-1 (HLA-A*02:01-positive) and OCI-Ly10 (HLA-A*02:01-negative) for 24 h, hPBls were stained for CD8 (BD) and murine constant TCRb region (mTCRβ) (Biolegend) and intracelluar IFNγ (BD) expression. Percentage of IFNγ-positive cells of CD8– and mTCRβ-positive cells is shown.

Figure 3:
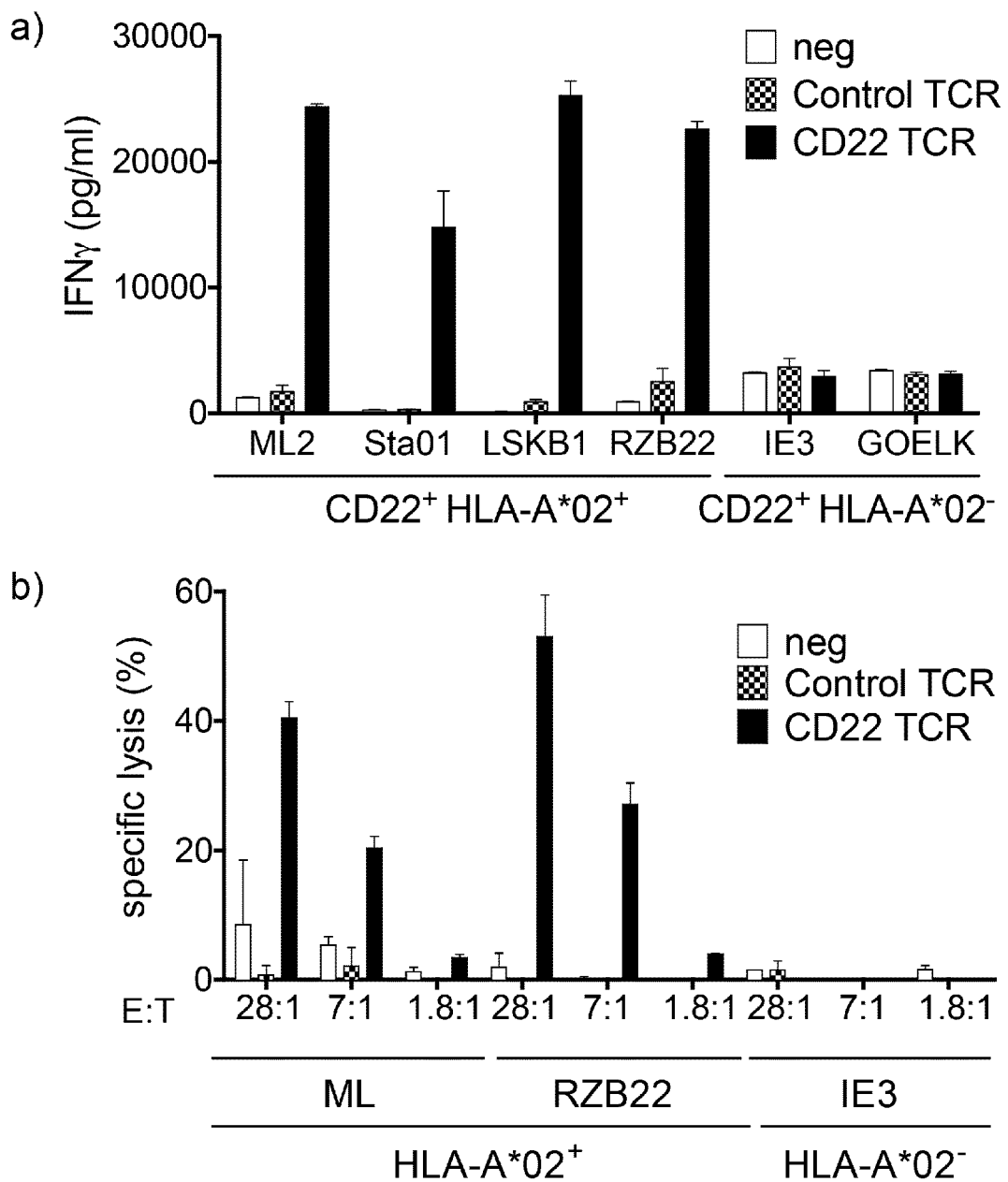
Figure 3:
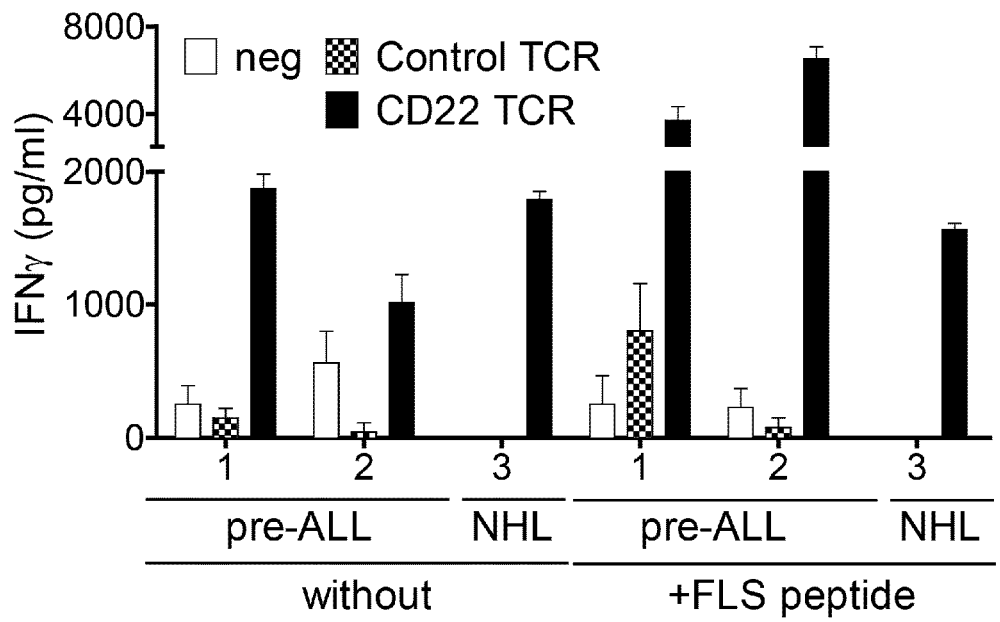

FIG. 3. CD22 recognizes a-b) HLA-A*02:01-positive lymphoblastoid cell lines (LCLs) and c) samples of two pre acute lymphoblastic leukemia (1, 2; pre ALL) and one Non-Hodgkin's lymphoma (3; NHL) patients. Human peripheral blood lymphocytes were retrovirally transduced with the CD22 TCR (black bar) or control TCR (checked bar) or were kept untransduced (neg; white bar) and were tested in a cocultivation assay with target cells. a), c) After 18-20 hours, IFNγ was detected in the cell supernatant by ELISA. The shown data is representative for at least two PBL donors. b) LCLs were used as targets in a standard-4-hour chromium release assay with different effector (TCR-positive T cells)-to-target (E:T) ratios. The shown data is representative for two PBL donors. c) Patient samples 1-3 were in addition loaded with the FLS peptide.

Figure 4:
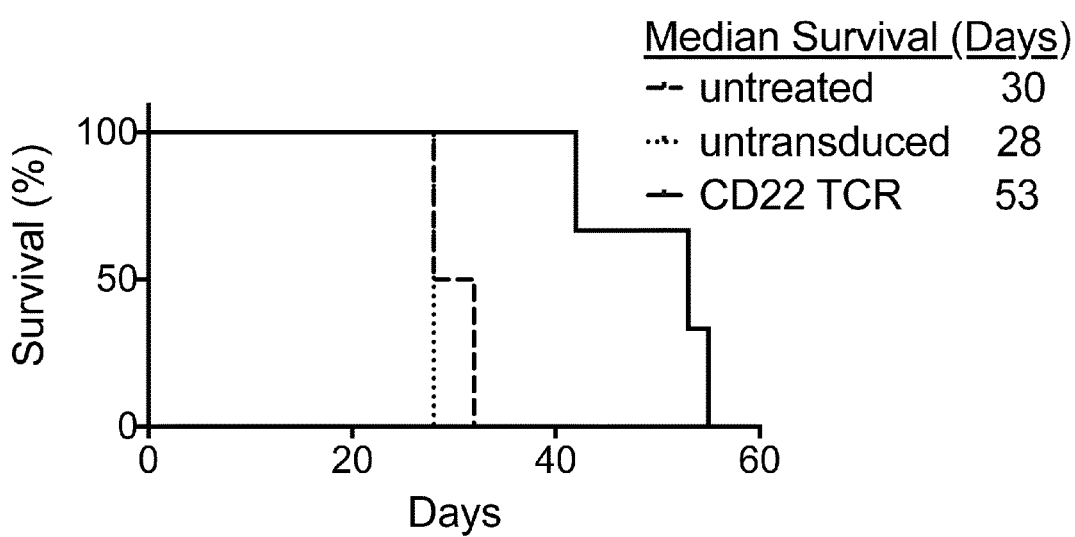

FIG. 4. CD22 TCR delays tumor growth in a xenograft mouse model. 5-6 weeks old female NOG mice were injected with 5×10^5 Nalm6 cells expressing firefly luciferase and CD90.1. On day 4, 5.6×10^6 hPBLs untransduced or transduced with CD22 TCR (39%) were injected i.v. into 3 mice per group. Two mice were left untreated. Mice were measured for luciferase signal on day 7, 14, 21, 28, 42 and 55. Blood was regularly taken and analyzed for tumor cells as well as transferred T cells. Body weight was regularly checked. a) Kaplan Meyer plot of survival and indicated median survival in days per group: untreated (long-dashed line), untransduced (short-dashed line) and CD22 TCR-transduced hPBLs (continues line).

Figure 5:
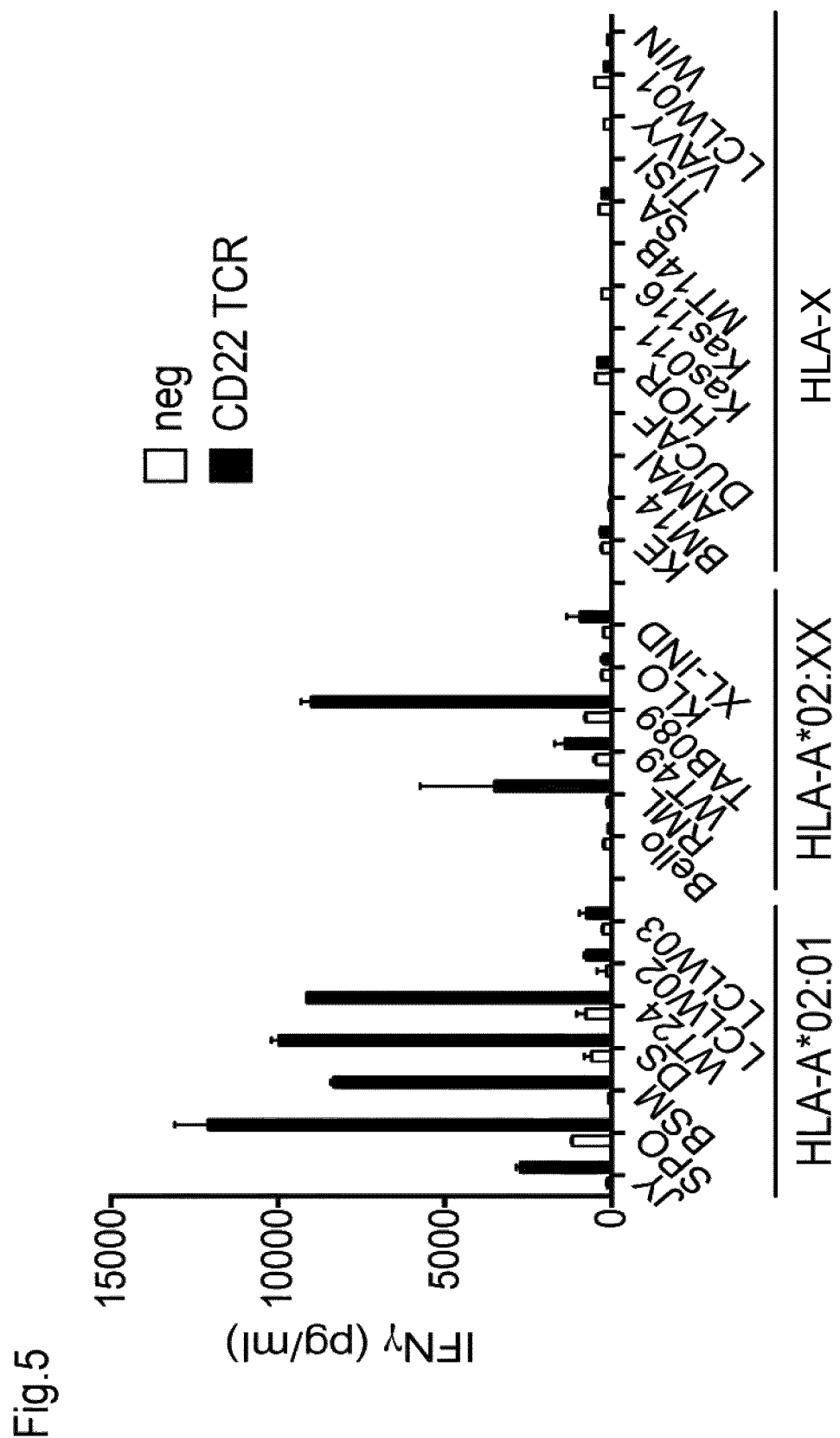

FIG. 5. CD22 TCR-transduced hPBLs were tested for alloreactivity with a panel of LCLs expressing CD22 and different HLA-subtypes. CD22 TCR does not show alloreactivity with other HLA-types (HLA-A*XX) but recognizes LCLs expressing HLA-A2 subtypes other than HLA-A*02: 01 (HLA-A*02:04, 05, 07, 10, and possibly other subtypes of HLA-A*02 but not HLA-A*02:02 and 08, cf. HLA-A*02:XX). CD22 TCR-transduced (black bar) or untransduced (neg; white bar) T cells were incubated with LCLs and subsequently, IFNγ was measured by ELISA after 18-20 h. The shown data is representative for three PBL donors.

Figure 6:
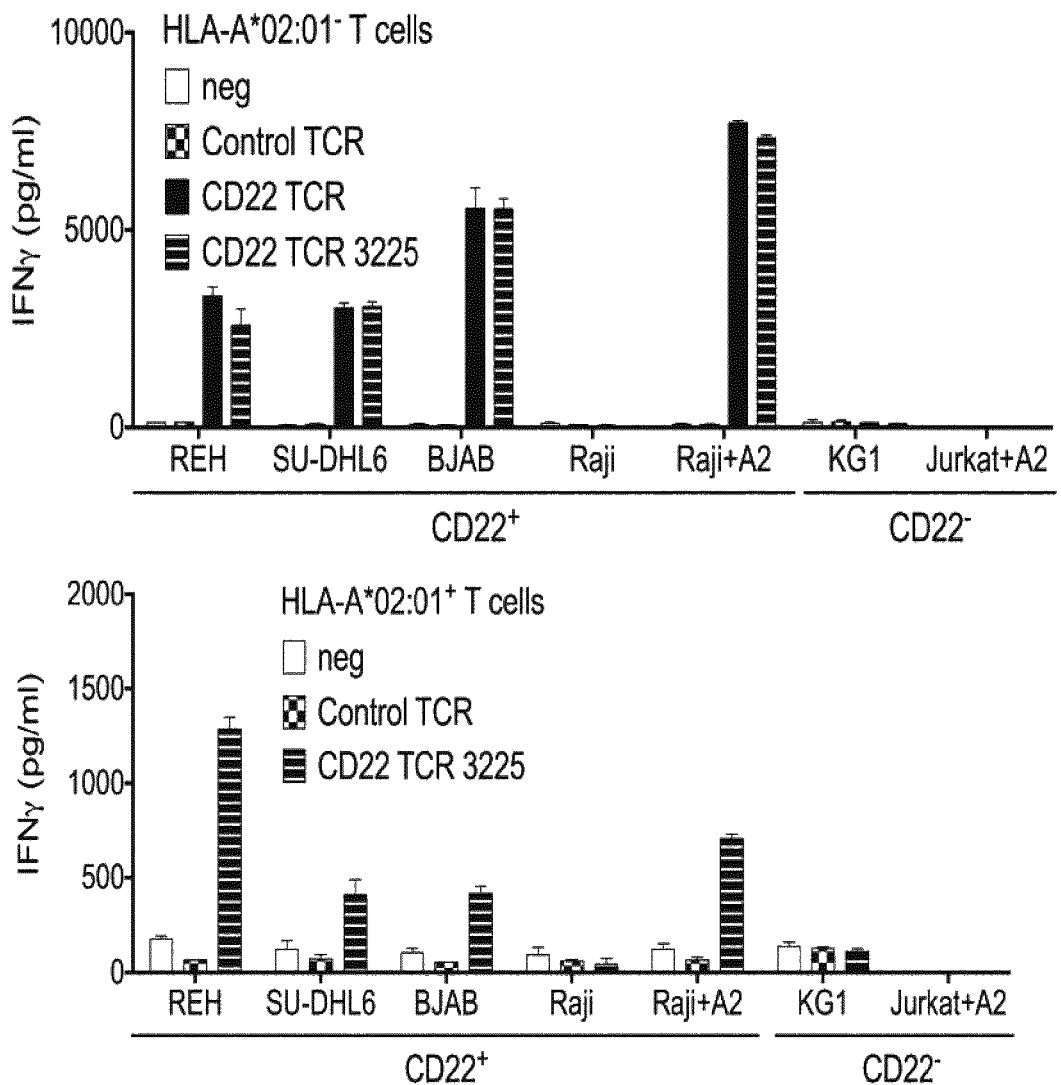
Figure 6:
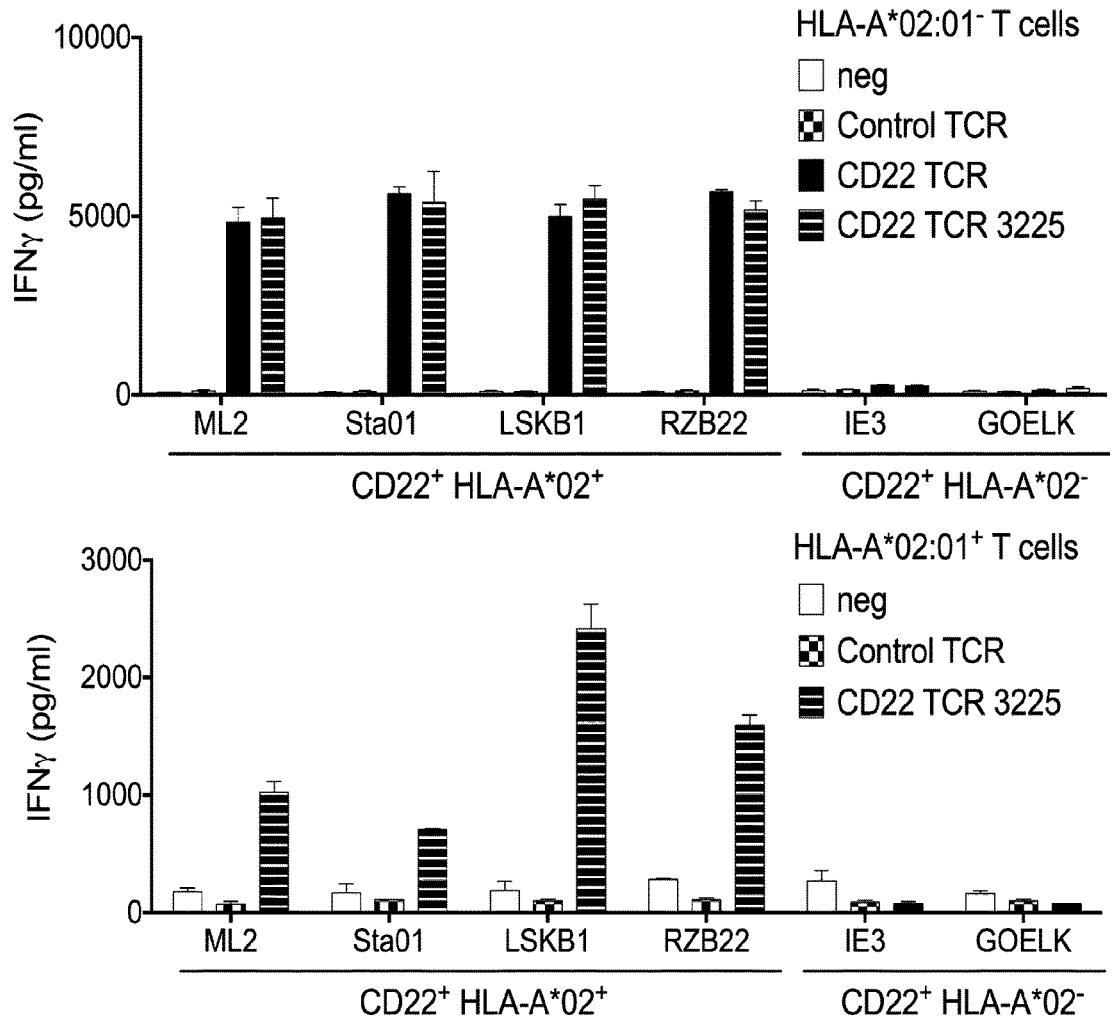
Figure 6:
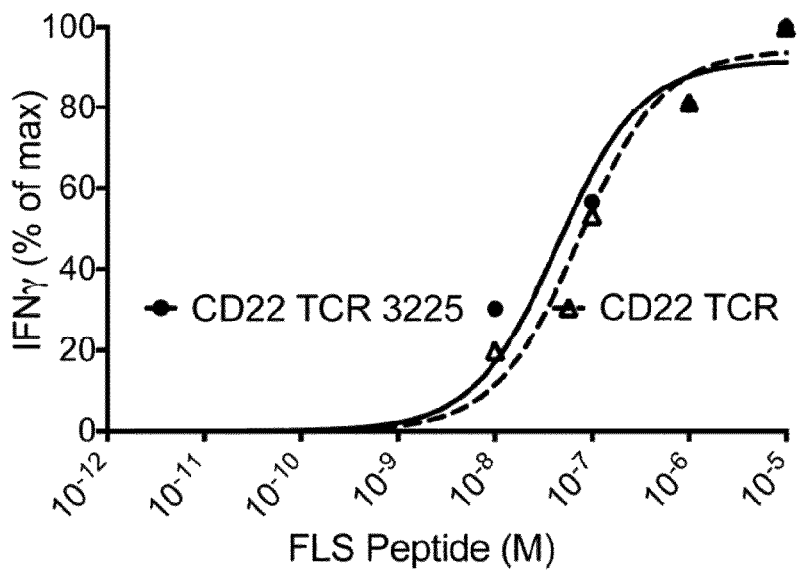

FIG. 6. Both CD22 TCR and CD22 TCR 3225 recognize a) different types of Hodgkin lymphoma and Pre-B-ALL that express CD22 and HLA-A*02:01 or diffuse large B cell lymphoma (DLBCL) line as well as Burkitt lymphoma cell lines that were genetically modified for HLA-A*02:01 expression and b) LCL cells expressing CD22 and HLA-A*02:01. a & b) Human peripheral blood lymphocytes (hPBLs) from HLA-A*02:01 negative (upper panels) or positive (lower panels) donor were retrovirally transduced with the CD22 TCR (black bar), CD22 TCR 3225 (striped bar) or control TCR (black dotted bar) or were untransduced (neg; white bar: negative control) and were tested in a cocultivation assay with target cells. After 18-20 hours, IFNγ was detected in the cell supernatant by ELISA. Representative data of one of three donors is shown.

In a), the Burkitt lymphoma cell line Raji normally does not express HLA-A2, so these cells are not recognized. In parallel, Raji cells were retrovirally transduced to obtain HLA-A*02:01 expression, and these cells are recognized. KG1 cells do not express either HLA-A2 or CD22 and are thus not recognized. Jurkat T cells transduced to express HLA-A*02:01 were not recognized, as they do not express CD22. In b), IE3 cells and GOELK express CD22, but not HLA-A2, so they are not recognized. The experiment in the upper panels, carried out with HLA-A2 negative host T cells, shows that CD22 TCR and CD22TCR 3225 have comparable functional avidity. The lower panel shows an additional confirmation experiment with the second CD22 TCR 3225 with HLA-A2 positive host T cells.

c) TCR-transduced hPBL of three donors were incubated with T2 cells loaded with titrated CD22 peptide of SEQ ID NO: 1 at an effector:target ratio of 1:1. After 18-20 h, IFNγ was determined in the cell supernatant by ELISA. The amount of IFNγ with 10 UM peptide-loaded T2 cells was set as 100%. The $K_d$ value of 2.2*10-8 for TCR 3225 was calculated with 50% of maximal IFNγ release. The curves and data points are the mean results of 3 individual donors. The experiment shows that the CD22 TCR 3225 has a still higher affinity than the first CD22 TCR.

EXAMPLES

Example 1: Generation of CD22 Specific TCR

T cells are negatively selected against self-antigens in the thymus to avoid autoimmune disease. To obtain a CD22-specific TCR, we used a mouse model that is transgenic for the human TCRα and TCRβ loci (Li, et al., 2010, Nat. Med.

16, 1029-35) to obtain murine T cells with human TCRs, as well as transgenic for the human HLA-A*02:01 for proper epitope presentation. After vaccination with the not homologous human CD22 cDNA by gene gun immunization, we achieved an immune response that was specific for CD22 tested by cocultivation of blood or spleen cells with NIH3T3 cells expressing the human HLA-A2 and CD22. Further evaluation of reactive T cells with a CD22-spanning peptide library and in silico predicted nonamers revealed the peptide specificity. This epitope was also described by Hassan et al. (2013, Mol Cell Proteomics 12 (7), 1829-43) who eluted it from LCLs. The herein described TCR was isolated from a mouse vaccinated four times by gene gun with full-length CD22 DNA. Splenocytes were cultured overnight with the corresponding peptide for an initial test of reactivity by intracellular IFNγ staining. The splenocytes were depleted for CD4 T cells, and non-CD4-T cells were cultured with 100 nM peptide for 10 days for the enrichment of specific T cells. On day 10, an IFNγ capture assay was performed and IFNγ-positive cells were sorted by FACS (FIG. 1a). RNA was isolated from sorted cells, cDNA synthesis and RACE-PCR performed followed by blunt-end TOPO cloning of the PCR fragments. TCR sequences were identified by Sanger sequencing and with help of the IMGT website. The identified variable TCR regions were synthesized as a codon-optimized sequence and molecularly cloned in combination with the murine constant regions and a peptide 2a linker between TCR chains into the γ-retroviral vector MP71 (FIG. 1b). The CD22 TCR was retrovirally transduced into human peripheral blood monocytes and expression was checked by staining with antibody against the murine constant TCRβ chain (FIG. 1c). Alternatively, it can be stained for its corresponding variable TCRβ chain, namely vβ2 according to Arden nomenclature. A peptide titration on T2 cells revealed a $K_d$ value of $1.1 \times 10^{-8}$ (FIG. 1d).

Example 2: CD22 TCR Confers Reactivity Towards CD22 Expressing Cell Lines and Primary Tumor Cells The CD22 TCR was tested for its reactivity towards recombinant and natural CD22 expressing cells. After TCR-transduction, human peripheral blood lymphocytes (hPBLs) were cocultivated with two renal cell carcinoma cell lines expressing CD22 as a full length version or as a truncated molecule missing the transmembrane and intracellular sequence but still comprising the epitope. The second CD22 version is only expressed intracellularly. 18-20 h later, supernatant of the coculture was tested for secreted IFNγ by ELISA. CD22 TCR-transduced hPBLs recognized both renal cell carcinoma cell lines expressing CD22 either in full length or as intracellular version (FIG. 2a). To further test the recognition of naturally CD22 expressing cells, CD22 TCR-transduced hPBLs were cocultured with a panel of B cell lines of different malignancies (FIG. 2b-d). Besides Hodgkin lymphoma (HDML2, L1236), Pre-B-ALL cells (Nalm6, REH), also Non-Hodgkin lymphoma like Burkitt lymphoma (BJAB, L591, Raji) and DLBCL (HBL-1) were recognized if they were also HLA-A*02:01-positive measured by secreted IFNγ (FIGS. 2b and c) or intracellular staining of IFNγ (FIG. 2d). L591 and Raji cells were only recognized if transduced with HLA-A*02:01. The DLBCL line OCI-Ly10 is HLA-A*02:01-negative and was not recognized. Also, in vitro immortalized primary B cells (lymphoblastic cell lines, LCLs) from HLA-A*02:01-positive healthy donors were recognized by CD22 TCR-transduced hPBLs as shown by INFγ secretion (FIG. 3a). In addition, they were killed in an effector-to-target ratio-dependent manner shown in a chromium release assay (FIG. 3b). LCLs that are HLA-A*02:01 negative were not recognized and killed. Cell samples expressing CD22 and HLA-A*02:01 derived from two pre-ALL (1 and 2) and one NHL (3) patient induced IFNγ secretion upon coculture. As positive control, samples were loaded with CD22 peptide (FIG. 3c).

Example 3: CD22 TCR Delays Tumor Growth in a Xenograft Mouse Model

To test the ability of CD22 TCR-transduced hPBLs to kill tumor cells in vivo, NOG mice were injected with the pre-ALL B cell line Nalm6 transduced with Firefly luciferase and the congenic marker CD90.1 and treated with hPBLs four days later. Tumor growth was measured by Firefly luciferase signal measurement and blood was analyzed for the congenic marker CD90.1 expressed by tumor cells and for transferred T cells by CD8 and TCRvβ chain staining. Median survival of mice transferred with CD22 TCR-transduced hPBLs was 53±7 days whereas mice that were left untreated or were transferred with untransduced hPBLs survived only 30±3 or 28±0 days, respectively (FIG. 4).

Example 4: Safety Analysis of CD22 TCR Recognition Profile

The CD22 TCR was shown to be very effective against CD22−/HLA-A*02:01-expressing tumor cells in vitro and in vivo. To see if CD22 TCR spares other normal cells not expressing CD22 and or other HLA types, several assays were conducted. First, to analyze a potential alloreactivity against other HLAs than HLA-A*02, CD22 TCR-transduced hPBLs were cocultivated with a panel of LCLs expressing a wide range of different HLA-types (Table 2a and b).

TABLE 2a

| HLA expression of tested LCLs (HLA-A, HLA-B, HLA-C) | | | | | | |
|---|---|---|---|---|---|---|
| LCL | HLA-A | | HLA-B | | HLA-C | |
| JY | 02:01 | | 07:02:01 | | 07:02:01:01 | |
| Bello | 02:02 | 11:01 | 41:01 | 52:01 | 12:02 | 17:01 |
| WT49 | 02:05:01 | | 58:01:01 | | 07:18 | |
| TAB089 | 02:07 | | 46:01 | | 01:02 | |
| KLO | 02:08 | 01:01:01:01 | 08:01:01 | 50:01:01 | 07:01:01:01 | 06:02:01:02 |
| XLI-ND | 02:10 | 30:01 | 13:02 | 40:06:01:01 | 06:02 | 08:01 |
| SPO | 02:01 | | 44:02 | | 05:01 | |
| KAS011 | 01:0101 | | 37:01 | | 06:02 | |
| BM14 | 03:01 | | 07:02 | | 07:02 | |
| MT14B | 31:01 | | 40:01 | | 03:04 | |
| SA | 24:020101 | | 07:0201 | | 07:02 | |

TABLE 2a-continued

HLA expression of tested LCLs (HLA-A, HLA-B, HLA-C)

| LCL | HLA-A | | HLA-B | | HLA-C | |
|---|---|---|---|---|---|---|
| HOR | 33:0301 | | 44:0301 | | 14:03 | |
| BSM | 02:0101 | | 15:010101 | | 03:0401 | |
| KE | 02:01 | 29:02 | 44:03 | 44:05 | 02:02 | 16:01 |
| TISI | 24:020101 | | 35:08 | | 04:01 | |
| WIN | 01:01 | | 57:0101 | | 06:02 | |
| KAS116 | 24:020101 | | 51:01 | | 12:03 | |
| DUCAF | 30:02 | | 18:01 | | 05:01 | |
| WT24 | 02:0101 | | 27:0502 | | 02:0202 | |
| AMAI | 68:02 | | 53:01 | | 04:01 | |
| VAVY | 01:01 | | 08:01 | | 07:01 | |
| RML | 02:04 | | 51:0101 | | 15:02 | |
| LCLW01 | 03:01 | 24:02 | 15:01 | 35:01 | 03:03 | 04:01 |
| LCLW02 | 02:01 | 26:01 | 38:01 | 44:02 | 05:01 | 12:03 |
| LCLW03 | 02:01 | 23:01 | 15:01 | 58:01 | 03:04 | 07:01 |

TABLE 2b

HLA expression of tested LCLs (DRB1, DQB1, DPB1)

| LCL | DRB1 | | DQB1 | | DPB1 | |
|---|---|---|---|---|---|---|
| JY | 04:04 | 13:01 | 03:02 | 06:03 | 02:01:02 | 04:01 |
| Bello | 04:05 | 08:04 | 2 | 4 | 03:01 | 104:01:00 |
| WT49 | 03:01:01 (17) | | 02:01:01 | | 04:01 | |
| TAB089 | 08:03:02 | | 06:01:01 | | 02:02 | |
| KLO | 03:01:01:01 | 07:01:01:01 | 02:01:01 | 02:02:01 | 01:01:01 | 104:01:00 |
| XLI-ND | 07:01:01 | 09:01:02 | 2 | 03:03 | 17:01 | 19:01 |
| SPO | 11:01 | | 05:02 | | 02:01:02 | |
| KAS011 | 16:01 | | 05:02 | | 04:01 | 14:01 |
| BM14 | 04:01 | | 03:02 | | 04:01 | |
| MT14B | 04:04 | | 03:02 | | 04:02 | |
| SA | | | | | 04:02 | |
| HOR | 13:02 | | 06:04 | | 04:01 | |
| BSM | 04:01 | | 03:02 | | 02:012 | |
| TISI | 11:03 | | 03:01 | | 04:02 | |
| WIN | 07:01 | | 02:01 | 03:03:02 | 04:01 | 13:01 |
| KAS116 | 01:01 | | 05:01 | | 13:01 | |
| DUCAF | 03:01 | | 02:01 | | 02:02 | |
| WT24 | | | | | 03:01 | |
| AMAI | 15:03 | | 06:02 | | 04:02 | |
| VAVY | 03:01 | | 02:01 | | 01:01 | |
| RML | 16:02 | | 03:01 | | 04:02 | |

IFNγ secretion was only observed when cocultivated with LCLs positive for HLA-A*02:01 and other certain HLA-A*02 subtypes (HLA-A*02:04, 05, 07, 10) since LCLs are CD22 positive, but no recognition of HLA-A*02:02 and 08 as well as of all other non-HLA-A2 types analyzed was seen (FIG. 5).

Example 5: CD22 TCR-3225 Confers Similar Reactivity Towards CD22 Expressing Cell Lines as CD22 TCR A second TCR was generated with the same method described in example 1. CD22 TCR 3225 comprises the same TCR vα chain as CD22 TCR, but its CDR3 region of the TCR vβ chain differs in two amino acids. The recognition of naturally processed CD22 epitope was shown in a coculture of TCR-transduced hPBLs with a panel of B cell lines of different malignancies (FIG. 6a) or EBV-immortalized B cells (LCLs) (FIG. 6b).

TCR-transduced hPBLs of a HLA-A2*02:01 negative (upper panel) or positive (lower panel) donor were cocultured with a panel of B cell lines of different malignancies (FIG. 6a). HLA-A*02:01 positive pre-B-ALL cells (REH), Non-Hodgkin lymphoma like Burkitt lymphoma (BJAB) and DLBCL (SU-DHL6) were recognized by CD22 TCR 3225 similar to CD22 TCR, and Burkitt lymphoma Raji cells were only recognized when they were transduced with HLA-A*02:01. CD22 negative cells (KG1 and Jurkat+ HLA-A*02:01) were not recognized. Lymphoblastic cell lines (LCLs) from HLA-A*02:01-positive healthy donors were recognized by CD22 TCR 3225 transduced hPBLs (HLA-A2*02:01-donor in upper panel/HLA-A2*02:01+ donor in lower panel) as shown by INFγ secretion (FIG. 6b).

The CD22 TCR and CD22 TCR 3225 were further tested for their affinity towards cognate peptide by a peptide-titration on T2 cells (FIG. 6c), and a $K_d$ value of $2.2 \times 10^{-8}$ was calculated for CD22 TCR 3225, i.e., the affinity is higher than the affinity of the CD22 TCR. T2 cells are TAPdeficient and thus do not present endogenous peptide. Exogenous peptide of SEQ ID NO: 1 was titrated on the T2 cells.

In general, $5*10-4$ target cells were and contacted with the $5*10-4$ TCR transduced hPBL T cells for 18-20 hours before INFγ in the supernatant was quantified by ELISA.

The invention claimed is:

1. A nucleic acid encoding at least one TCR alpha or beta chain construct of a TCR construct capable of specifically binding to a peptide of SEQ ID NO: 1 in the context of HLA-A*02,
- i) wherein the TCR alpha chain construct comprises a CDR1 sequence having SEQ ID NO: 2, a CDR2 sequence having SEQ ID NO: 3, and a CDR3 sequence having a sequence identity of at least 83% to SEQ ID NO: 4; and/or
- ii) wherein the TCR beta chain construct comprises
  - a) a CDR1 sequence having SEQ ID NO: 20, a CDR2 sequence having SEQ ID NO: 21, and a CDR3 sequence having a sequence identity of at least 83% to SEQ ID NO: 22, or
  - b) a CDR1 sequence having SEQ ID NO: 5, a CDR2 sequence having SEQ ID NO: 6 and a CDR3 sequence having a sequence identity of at least 83% to SEQ ID NO: 7, wherein in the TCR beta chain construct, only positions 5 and 6 of the CDR3 may be mutated, wherein a mutation in this position is a substitution.

2. The nucleic acid of claim 1, wherein the TCR alpha chain construct comprises a CDR1 sequence having a sequence as set forth in SEQ ID NO: 2, a CDR2 sequence having a sequence as set forth in SEQ ID NO: 3 and a CDR3 sequence having a sequence as set forth in SEQ ID NO: 4, and/or wherein the TCR beta chain construct comprises a CDR1 sequence having a sequence as set forth in SEQ ID NO: 20, a CDR2 sequence having a sequence as set forth in SEQ ID NO: 21 and a CDR3 sequence having a sequence as set forth in SEQ ID NO: 22.

3. The nucleic acid of claim 1, wherein the TCR alpha chain construct comprises a variable region having a sequence identity of at least 90% to SEQ ID NO: 16 without aa 1-20, and/or wherein the TCR beta chain construct comprises a variable region having a sequence identity of at least 90% to SEQ ID NO: 25 without aa 1-14.

4. The nucleic acid of claim 1, wherein the TCR alpha chain construct comprises a CDR1 sequence having a sequence as set forth in SEQ ID NO: 2, a CDR2 sequence having a sequence as set forth in SEQ ID NO: 3 and a CDR3 sequence having a sequence as set forth in SEQ ID NO: 4, and/or wherein the TCR beta chain construct comprises a CDR1 sequence having a sequence identity of identity of as set forth in SEQ ID NO: 5, a CDR2 sequence having a sequence as set forth in SEQ ID NO: 6 and a CDR3 sequence having a sequence as set forth in SEQ ID NO: 7.

5. The nucleic acid of claim 1, wherein the sequence identity to the recited CDR1 and CDR2 and CDR3 is 100%.

6. The nucleic acid of claim 1, wherein the TCR alpha chain construct and/or the TCR beta chain construct further comprise a constant region selected from the group comprising a human constant region, a murine constant region or a chimeric constant region.

7. The nucleic acid of claim 1, encoding at least one TCR alpha and beta chain construct of the TCR construct.

8. The nucleic acid of claim 1, which is a viral vector, a transposon, a vector suitable for CRISPR/CAS based recombination or a plasmid suitable for in vitro RNA transcription.

9. The nucleic acid of claim 1, which further encodes a cell surface protein selected from the group consisting of CD20 and truncated epithelial growth factor (EGF) receptor under the control of a promotor suitable for expression of the cell surface protein in a T cell.

10. The nucleic acid of claim 1, wherein the TCR beta chain construct comprises a CDR1, CDR2, and CDR2 as set forth in SEQ ID NO: 20, SEQ ID NO: 21, and SEQ ID NO: 22, respectively.

11. The nucleic acid of claim 1, wherein the TCR beta chain construct comprises
   a) a CDR1 sequence having SEQ ID NO: 20, a CDR2 sequence having SEQ ID NO: 21 and a CDR3 sequence having a sequence identity of SEQ ID NO: 22, or
   b) wherein the TCR beta chain construct comprises a CDR1 sequence having SEQ ID NO: 5, a CDR2 sequence having SEQ ID NO: 6 and a CDR3 sequence having SEQ ID NO: 7.

12. The nucleic acid of claim 11, encoding at least one TCR alpha and beta chain construct of the TCR construct.

13. A pharmaceutical composition comprising a nucleic acid of claim 1 encoding a TCR construct that specifically binds to a peptide of SEQ ID NO: 1 in the context of HLA-A*02.

14. A host cell comprising a nucleic acid of claim 1.

15. A host cell of claim 14, wherein the host cell is a human CD8+ T cell.

16. A pharmaceutical composition comprising the host cell of claim 15; wherein the host cell expresses a TCR construct that specifically binds to a peptide of SEQ ID NO: 1 in the context of HLA-A*02.

17. A protein encoded by the nucleic acid of claim 1.

18. A pharmaceutical composition comprising the protein of claim 17; wherein the protein comprises a TCR construct that specifically binds to a peptide of SEQ ID NO: 1 in the context of HLA-A*02.

19. A host cell comprising the protein of claim 17.

20. A method of treating B cell lymphoma or B cell leukemia in a patient comprising administering to the subject the pharmaceutical composition of claim 13, wherein the patient expresses HLA-A*02.

21. The method of treating a B cell lymphoma or B cell leukemia of claim 20, wherein the patient has a relapsed or primary refractory B cell lymphoma or B cell leukemia.

22. The method of claim 20, wherein the patient has diffuse large B-cell lymphoma.

23. An immunotherapy comprising administering to the subject the pharmaceutical composition of claim 13, wherein the immunotherapy comprises adoptive T cell therapy or TCR gene therapy.

* * * * *